(12) United States Patent
Chen et al.

(10) Patent No.: US 8,956,841 B2
(45) Date of Patent: Feb. 17, 2015

(54) RECOMBINANT REVERSE TRANSCRIPTASES

(71) Applicant: Applied Biosystems, LLC, Carlsbad, CA (US)

(72) Inventors: Liangjing Chen, Austin, TX (US); Robert Setterquist, Austin, TX (US); Gary Latham, Austin, TX (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

(21) Appl. No.: 13/730,108

(22) Filed: Dec. 28, 2012

(65) Prior Publication Data

US 2013/0189758 A1    Jul. 25, 2013

Related U.S. Application Data

(63) Continuation of application No. 12/568,364, filed on Sep. 28, 2009, now Pat. No. 8,361,754, which is a continuation of application No. 10/827,498, filed on Apr. 19, 2004, now Pat. No. 7,595,179.

(51) Int. Cl.
*C12N 9/12* (2006.01)
*C07H 21/04* (2006.01)

(52) U.S. Cl.
CPC .................................. *C12N 9/1276* (2013.01)
USPC .......... 435/194; 435/183; 536/23.1; 536/23.2

(58) Field of Classification Search
None
See application file for complete search history.

(56) References Cited

U.S. PATENT DOCUMENTS

| | | | |
|---|---|---|---|
| 4,663,290 | A | 5/1987 | Weis et al. |
| 4,683,195 | A | 7/1987 | Mullis et al. |
| 4,683,202 | A | 7/1987 | Mullis |
| 4,943,531 | A | 7/1990 | Goff et al. |
| 4,965,188 | A | 10/1990 | Mullis et al. |
| 5,017,492 | A | 5/1991 | Kotewicz et al. |
| 5,219,727 | A | 6/1993 | Wang et al. |
| 5,244,797 | A | 9/1993 | Kotewicz et al. |
| 5,540,776 | A | 7/1996 | Habsburg-Lothringen |
| 5,668,005 | A | 9/1997 | Kotewicz et al. |
| 5,891,637 | A | 4/1999 | Ruppert |
| 5,998,195 | A | 12/1999 | Kacian et al. |
| 6,063,608 | A | 5/2000 | Kotewicz et al. |
| 6,136,582 | A | 10/2000 | Gao et al. |
| 6,391,607 | B1 | 5/2002 | Lazarus et al. |
| 6,440,412 | B1 | 8/2002 | Frenz et al. |
| 6,589,768 | B1 | 7/2003 | Kotewicz et al. |
| 6,610,522 | B1 | 8/2003 | Kotewicz et al. |
| 6,630,333 | B1 | 10/2003 | Hughes, Jr. |
| 7,056,716 | B2 | 6/2006 | Potter et al. |
| 7,078,208 | B2 | 7/2006 | Smith et al. |
| 7,595,179 | B2 | 9/2009 | Chen et al. |
| 8,361,754 | B2 | 1/2013 | Chen et al. |
| 2007/0141592 | A1 | 6/2007 | Smith et al. |

FOREIGN PATENT DOCUMENTS

| | | |
|---|---|---|
| WO | WO01/68895 | 9/2001 |
| WO | WO01/92500 | 12/2001 |
| WO | WO2004/024749 | 3/2004 |

OTHER PUBLICATIONS

Goedken et al., "Folding the Ribonuclease H Domain of Moloney Murine Leukemia Virus Reverse Transcriptase Requires Metal Binding or a Short N-terminal Extension", *Proteins: Structure, Function, and Genetics*, vol. 33, Oct. 1998, 135-143.
Ngo et al., "Computational Complexity, Protein Structure Prediction, and Levinthal Paradox", *The Protein Folding Problem and Tertiary Structure Prediction: Birkhauser*, Boston, MA, 1994, 433 and 492-495.
International Application No. PCT/US2005/012671, International Search Report and Written Opinion, Jun. 19, 2008.
Pfeiffer et al., "Structure-Based Moloney Murine Leukemia Virus Reverse Transcriptase Mutants with Altered Intracellular Direct-Repeat Deletion Frequencies", *Journal of Virology*, vol. 74, No. 20, Oct. 2000, 9629-9636.
Unknown, "Score Search Results Details for Application No. 10827498", http://es/ScoreAccessWeb/GetItem.action?Appld=10827498&seqId=09323b67805aa350&I, 2, Jan. 4, 2009.

*Primary Examiner* — Richard Hutson

(57) ABSTRACT

The present invention relates to a gene that encodes a hyperactive reverse transcriptase having DNA polymerase activity and substantially reduced RNase H activity, vectors containing the gene and host cells transformed with the invention. The present invention also includes a method of producing the hyperactive reverse transcriptase, producing cDNA from mRNA using the reverse transcriptase of the invention, kits and assay templates made using the hyperactive reverse transcriptase.

7 Claims, 6 Drawing Sheets

Figure 1.

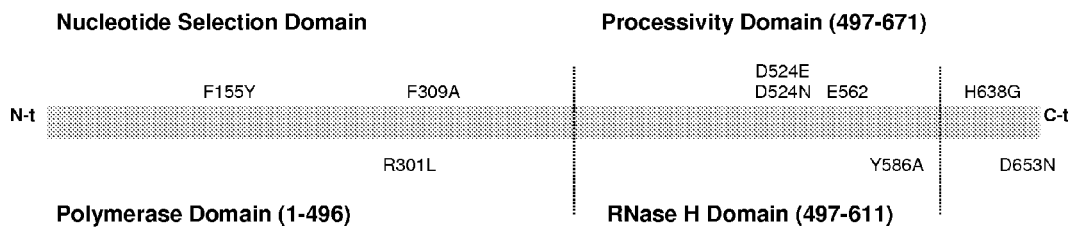

Figure 2.

```
ATGACCCTAAATATAGAAGATGAGTATCGGCTACATGAGACCTCAAAAGAGCCAGATGTTTCTCTAGGGTCC
ACATGGCTGTCTGATTTTCCTCAGGCCTGGGCGGAAACCGGGGGCATGGGACTGGCAGTTCGCCAAGCTCCT
CTGATCATACCTCTGAAAGCAACCTCTACCCCCGTGTCCATAAAACAATACCCCATGTCACAAGAAGCCAGA
CTGGGGATCAAGCCCCACATACAGAGACTGTTGGACCAGGGAATACTGGTACCCTGCCAGTCCCCCTGGAAC
ACGCCCCTGCTACCCGTTAAGAAACCAGGGACTAATGATTATAGGCCTGTCCAGGATCTGAGAGAAGTCAAC
AAGCGGGTGGAAGACATCCACCCCACCGTGCCCAACCCTTACAACCTCTTGAGCGGGCTCCACCGTCCCAC
CAGTGGTACACTGTGCTTGATTTAAAGGATGCCTATTTCTGCCTGAGACTCCACCCCACCAGTCAGCCTCTC
TTCGCCTTTGAGTGGAGAGATCCAGAGATGGGAATCTCAGGACAATTGACCTGGACCAGACTCCCACAGGGT
TTCAAAAACAGTCCCACCCTGTTTGATGAGGCACTGCACAGAGACCTAGCAGACTTCCGGATCCAGCACCCA
GACTTGATCCTGCTACAGTACGTGGATGACTTACTGCTGGCCGCCACTTCTGAGCTAGACTGCCAACAAGGT
ACTCGGGCCCTGTTACAAACCCTAGGGAACCTCGGGTATCGGGCCTCGGCCAAGAAAGCCCAAATTTGCCAG
AAACAGGTCAAGTATCTGGGGTATCTTCTAAAAGAGGGTCAGAGATGGCTGACTGAGGCCAGAAAAGAGACT
GTGATGGGGCAGCCTACTCCGAAGACCCCTCGACAACTAAGGGAGTTCCTAGGGACGGCAGGCTTCTGTCGC
CTCTGGATCCCTGGGTTTGCAGAAATGGCAGCCCCCTTGTACCCTCTCACCAAAACGGGGACTCTGTTTAAT
TGGGGCCCAGACCAACAAAAGGCCTATCAAGAAATCAAGCAAGCTCTTCTAACTGCCCCAGCCCTGGGGTTG
CCAGATTTGACTAAGCCCTTTGAACTCTTTGTCGACGAGAAGCAGGGCTACGCCAAAGGTGTCCTAACGCAA
AAACTGGGACCTTGGCGTCGGCCGGTGGCCTACCTGTCCAAAAAGCTAGACCCAGTAGCAGCTGGGTGGCCC
CCTTGCCTACGGATGGTAGCAGCCATTGCCGTACTGACAAAGGATGCAGGCAAGCTAACCATGGGACAGCCA
CTAGTCATTCTGGCCCCCCCATGCAGTAGAGGCACTAGTCAAACAACCCCCCGACCGCTGGCTTTCCAACGCC
CGGATGACTCACTATCAGGCCTTGCTTTTGGACACGGACCGGGTCCAGTTCGGACCGGTGGTAGCCCTGAAC
CCGGCTACGCTGCTCCCACTGCCTGAGGAAGGGCTGCAACACAACTGCCTTGATATCCTGGCCGAAGCCCAC
GGAACCCGACCCGACCTAACGGACCAGCCGCTCCCAGACGCCGACCACACCTGGTACACGGATGGAAGCAGT
CTCTTACAAGAGGGACAGCGTAAGGCGGGAGCTGCGGTGACCACCGAGACCGAGGTAATCTGGGCTAAAGCC
CTGCCAGCCGGGACATCCGCTCAGCGGGCTGAACTGATAGCACTCACCCAGGCCCTAAAGATGGCAGAAGGT
AAGAAGCTAAATGTTTATACTGATAGCCGTTATGCTTTTGCTACTGCCCATATCCATGGAGAAATATACAGA
AGGCGTGGGTTGCTCACATCAGAAGGCAAAGAGATCAAAAATAAAGACGAGATCTTGGCCCTACTAAAAGCC
CTCTTTCTGCCCAAAAGACTTAGCATAATCCATTGTCCCGGGGGTCAAAAGGGACACAGCGCCGAGGCTAG
AGGCAACCGGATGGCTGACCAAGCGGCCCGAAAGGCAGCCATCACAGAGACTCCAGACACCTCTACCCTCCT
CCACCACCACCACCACCACTAA
```

Figure 3.

```
MTLNIEDEYRLHETSKEPDVSLGSTWLSDFPQAWAETGGMGLAVRQAPLIIPLKATSTPVSIKQYPMSQEAR
LGIKPHIQRLLDQGILVPCQSPWNTPLLPVKKPGTNDYRPVQDLREVNKRVEDIHPTVPNPYNLLSGLPPSH
QWYTVLDLKDAYFCLRLHPTSQPLFAFEWRDPEMGISGQLTWTRLPQGFKNSPTLFDEALHRDLADFRIQHP
DLILLQYVDDLLLAATSELDCQQGTRALLQTLGNLGYRASAKKAQICQKQVKYLGYLLKEGQRWLTEARKET
VMGQPTPKTPRQLREFLGTAGFCRLWIPGFAEMAAPLYPLTKTGTLFNWGPDQQKAYQEIKQALLTAPALGL
PDLTKPFELFVDEKQGYAKGVLTQKLGPWRRPVAYLSKKLDPVAAGWPPCLRMVAAIAVLTKDAGKLTMGQP
LVILAPHAVEALVKQPPDRWLSNARMTHYQALLLDTDRVQFGPVVALNPATLLPLPEEGLQHNCLDILAEAH
GTRPDLTDQPLPDADHTWYTDGSSLLQEGQRKAGAAVTTETEVIWAKALPAGTSAQRAELIALTQALKMAEG
KKLNVYTDSRYAFATAHIHGEIYRRRGLLTSEGKEIKNKDEILALLKALFLPKRLSIIHCPGGQKGHSAEAR
GNRMADQAARKAAITETPDTSTLLHHHHHH
```

Figure 4.

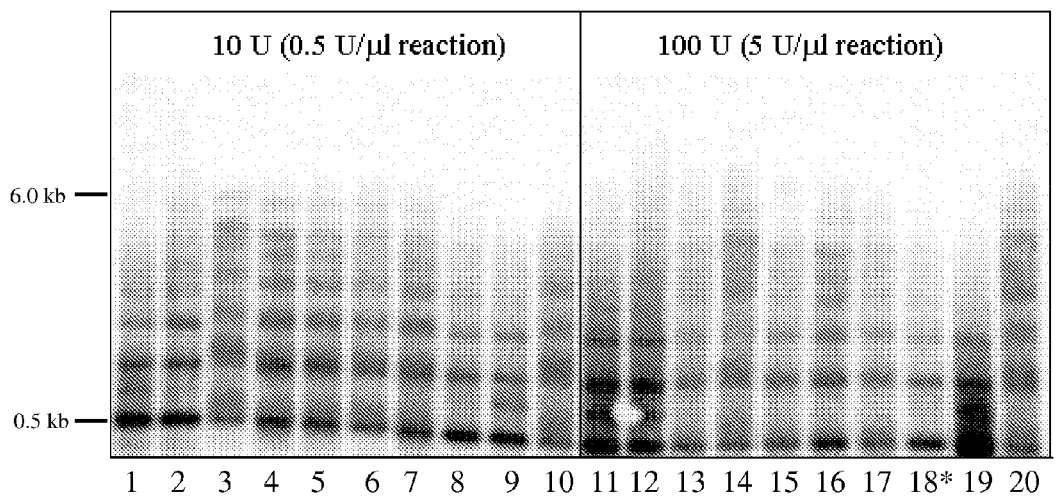

L. DNA 10kb ladder
1. Superscript II
2. wt MMLV
3. F155Y/H638G
4. F155Y
5. H638G
6. D524N
7. E562D
8. D653N
9. D524E One round RNA amplification with 100 ng Rat Thymus total RNA

| Sample ID | aRNA Yield (ug) |
|---|---|
| 1000ng_SS II | 63.9 |
| 1000ng_SS II | 50.8 |
| 100ng_SS II | 7.7 |
| 100ng_SS II | 7.7 |
| 1000ng_DM | 56.6 |
| 1000ng_DM | 66.2 |
| 100ng_DM | 9.6 |
| 100ng_DM | 8.8 |

SEQUENCE LISTING

```
<160> NUMBER OF SEQ ID NOS: 20

<210> SEQ ID NO 1
<211> LENGTH: 2037
<212> TYPE: DNA
<213> ORGANISM: Moloney murine sarcoma virus
<220> FEATURE:
<221> NAME/KEY: CDS
<222> LOCATION: (1)..(2037)

<400> SEQUENCE: 1 atg acc cta aat ata gaa gat gag tat cgg cta cat gag acc tca aaa      48
Met Thr Leu Asn Ile Glu Asp Glu Tyr Arg Leu His Glu Thr Ser Lys
1               5                   10                  15 gag cca gat gtt tct cta ggg tcc aca tgg ctg tct gat ttt cct cag      96
Glu Pro Asp Val Ser Leu Gly Ser Thr Trp Leu Ser Asp Phe Pro Gln
            20                  25                  30 gcc tgg gcg gaa acc ggg ggc atg gga ctg gca gtt cgc caa gct cct     144
Ala Trp Ala Glu Thr Gly Gly Met Gly Leu Ala Val Arg Gln Ala Pro
        35                  40                  45 ctg atc ata cct ctg aaa gca acc tct acc ccc gtg tcc ata aaa caa     192
Leu Ile Ile Pro Leu Lys Ala Thr Ser Thr Pro Val Ser Ile Lys Gln
    50                  55                  60 tac ccc atg tca caa gaa gcc aga ctg ggg atc aag ccc cac ata cag     240
Tyr Pro Met Ser Gln Glu Ala Arg Leu Gly Ile Lys Pro His Ile Gln
65                  70                  75                  80 aga ctg ttg gac cag gga ata ctg gta ccc tgc cag tcc ccc tgg aac     288
Arg Leu Leu Asp Gln Gly Ile Leu Val Pro Cys Gln Ser Pro Trp Asn
                85                  90                  95 acg ccc ctg cta ccc gtt aag aaa cca ggg act aat gat tat agg cct     336
Thr Pro Leu Leu Pro Val Lys Lys Pro Gly Thr Asn Asp Tyr Arg Pro
            100                 105                 110 gtc cag gat ctg aga gaa gtc aac aag cgg gtg gaa gac atc cac ccc     384
Val Gln Asp Leu Arg Glu Val Asn Lys Arg Val Glu Asp Ile His Pro
        115                 120                 125 acc gtg ccc aac cct tac aac ctc ttg agc ggg ctc cca ccg tcc cac     432
Thr Val Pro Asn Pro Tyr Asn Leu Leu Ser Gly Leu Pro Pro Ser His
    130                 135                 140 cag tgg tac act gtg ctt gat tta aag gat gcc tat ttc tgc ctg aga     480
Gln Trp Tyr Thr Val Leu Asp Leu Lys Asp Ala Tyr Phe Cys Leu Arg
145                 150                 155                 160 ctc cac ccc acc agt cag cct ctc ttc gcc ttt gag tgg aga gat cca     528
Leu His Pro Thr Ser Gln Pro Leu Phe Ala Phe Glu Trp Arg Asp Pro
                165                 170                 175 gag atg gga atc tca gga caa ttg acc tgg acc aga ctc cca cag ggt     576
Glu Met Gly Ile Ser Gly Gln Leu Thr Trp Thr Arg Leu Pro Gln Gly
            180                 185                 190 ttc aaa aac agt ccc acc ctg ttt gat gag gca ctg cac aga gac cta     624
Phe Lys Asn Ser Pro Thr Leu Phe Asp Glu Ala Leu His Arg Asp Leu
        195                 200                 205 gca gac ttc cgg atc cag cac cca gac ttg atc ctg cta cag tac gtg     672
```

```
Ala Asp Phe Arg Ile Gln His Pro Asp Leu Ile Leu Leu Gln Tyr Val
        210                 215                 220 gat gac tta ctg ctg gcc gcc act tct gag cta gac tgc caa caa ggt       720
Asp Asp Leu Leu Leu Ala Ala Thr Ser Glu Leu Asp Cys Gln Gln Gly
225                 230                 235                 240 act cgg gcc ctg tta caa acc cta ggg aac ctc ggg tat cgg gcc tcg       768
Thr Arg Ala Leu Leu Gln Thr Leu Gly Asn Leu Gly Tyr Arg Ala Ser
                245                 250                 255 gcc aag aaa gcc caa att tgc cag aaa cag gtc aag tat ctg ggg tat       816
Ala Lys Lys Ala Gln Ile Cys Gln Lys Gln Val Lys Tyr Leu Gly Tyr
            260                 265                 270 ctt cta aaa gag ggt cag aga tgg ctg act gag gcc aga aaa gag act       864
Leu Leu Lys Glu Gly Gln Arg Trp Leu Thr Glu Ala Arg Lys Glu Thr
        275                 280                 285 gtg atg ggg cag cct act ccg aag acc cct cga caa cta agg gag ttc       912
Val Met Gly Gln Pro Thr Pro Lys Thr Pro Arg Gln Leu Arg Glu Phe
290                 295                 300 cta ggg acg gca ggc ttc tgt cgc ctc tgg atc cct ggg ttt gca gaa       960
Leu Gly Thr Ala Gly Phe Cys Arg Leu Trp Ile Pro Gly Phe Ala Glu
305                 310                 315                 320 atg gca gcc ccc ttg tac cct ctc acc aaa acg ggg act ctg ttt aat      1008
Met Ala Ala Pro Leu Tyr Pro Leu Thr Lys Thr Gly Thr Leu Phe Asn
                325                 330                 335 tgg ggc cca gac caa caa aag gcc tat caa gaa atc aag caa gct ctt      1056
Trp Gly Pro Asp Gln Gln Lys Ala Tyr Gln Glu Ile Lys Gln Ala Leu
            340                 345                 350 cta act gcc cca gcc ctg ggg ttg cca gat ttg act aag ccc ttt gaa      1104
Leu Thr Ala Pro Ala Leu Gly Leu Pro Asp Leu Thr Lys Pro Phe Glu
        355                 360                 365 ctc ttt gtc gac gag aag cag ggc tac gcc aaa ggt gtc cta acg caa      1152
Leu Phe Val Asp Glu Lys Gln Gly Tyr Ala Lys Gly Val Leu Thr Gln
370                 375                 380 aaa ctg gga cct tgg cgt cgg ccg gtg gcc tac ctg tcc aaa aag cta      1200
Lys Leu Gly Pro Trp Arg Arg Pro Val Ala Tyr Leu Ser Lys Lys Leu
385                 390                 395                 400 gac cca gta gca gct ggg tgg ccc cct tgc ctc cgg atg gta gca gcc      1248
Asp Pro Val Ala Ala Gly Trp Pro Pro Cys Leu Arg Met Val Ala Ala
                405                 410                 415 att gcc gta ctg aca aag gat gca ggc aag cta acc atg gga cag cca      1296
Ile Ala Val Leu Thr Lys Asp Ala Gly Lys Leu Thr Met Gly Gln Pro
            420                 425                 430 cta gtc att ctg gcc ccc cat gca gta gag gca cta gtc aaa caa ccc      1344
Leu Val Ile Leu Ala Pro His Ala Val Glu Ala Leu Val Lys Gln Pro
        435                 440                 445 ccc gac cgc tgg ctt tcc aac gcc cgg atg act cac tat cag gcc ttg      1392
Pro Asp Arg Trp Leu Ser Asn Ala Arg Met Thr His Tyr Gln Ala Leu
450                 455                 460 ctt ttg gac acg gac cgg gtc cag ttc gga ccg gtg gta gcc ctg aac      1440
Leu Leu Asp Thr Asp Arg Val Gln Phe Gly Pro Val Val Ala Leu Asn
465                 470                 475                 480 ccg gct acg ctg ctc cca ctg cct gag gaa ggg ctg caa cac aac tgc      1488
Pro Ala Thr Leu Leu Pro Leu Pro Glu Glu Gly Leu Gln His Asn Cys
                485                 490                 495 ctt gat atc ctg gcc gaa gcc cac gga acc cga ccc gac cta acg gac      1536
Leu Asp Ile Leu Ala Glu Ala His Gly Thr Arg Pro Asp Leu Thr Asp
            500                 505                 510 cag cct ctc cca gac gcc gac cac acc tgg tac acg gat gga agc agt      1584
Gln Pro Leu Pro Asp Ala Asp His Thr Trp Tyr Thr Asp Gly Ser Ser
        515                 520                 525
```

-continued

| | | |
|---|---|---|
| ctc tta caa gag gga cag cgt aag gcg gga gct gcg gtg acc acc gag<br>Leu Leu Gln Glu Gly Gln Arg Lys Ala Gly Ala Ala Val Thr Thr Glu<br>530     535     540 | 1632 |
| acc gag gta atc tgg gct aaa gcc ctg cca gcc ggg aca tcc gct cag<br>Thr Glu Val Ile Trp Ala Lys Ala Leu Pro Ala Gly Thr Ser Ala Gln<br>545    550     555     560 | 1680 |
| cgg gct gaa ctg ata gca ctc acc cag gcc cta aag atg gca gaa ggt<br>Arg Ala Glu Leu Ile Ala Leu Thr Gln Ala Leu Lys Met Ala Glu Gly<br>     565     570     575 | 1728 |
| aag aag cta aat gtt tat act gat agc cgt tat gct ttt gct act gcc<br>Lys Lys Leu Asn Val Tyr Thr Asp Ser Arg Tyr Ala Phe Ala Thr Ala<br>    580     585     590 | 1776 |
| cat atc cat gga gaa ata tac aga agg cgt ggg ttg ctc aca tca gaa<br>His Ile His Gly Glu Ile Tyr Arg Arg Arg Gly Leu Leu Thr Ser Glu<br>595     600     605 | 1824 |
| ggc aaa gag atc aaa aat aaa gac gag atc ttg gcc cta cta aaa gcc<br>Gly Lys Glu Ile Lys Asn Lys Asp Glu Ile Leu Ala Leu Leu Lys Ala<br>610     615     620 | 1872 |
| ctc ttt ctg ccc aaa aga ctt agc ata atc cat tgt ccc ggg ggt caa<br>Leu Phe Leu Pro Lys Arg Leu Ser Ile Ile His Cys Pro Gly Gly Gln<br>625     630     635     640 | 1920 |
| aag gga cac agc gcc gag gct aga ggc aac cgg atg gct gac caa gcg<br>Lys Gly His Ser Ala Glu Ala Arg Gly Asn Arg Met Ala Asp Gln Ala<br>     645     650     655 | 1968 |
| gcc cga aag gca gcc atc aca gag act cca gac acc tct acc ctc ctc<br>Ala Arg Lys Ala Ala Ile Thr Glu Thr Pro Asp Thr Ser Thr Leu Leu<br>    660     665     670 | 2016 |
| cac cac cac cac cac cac taa<br>His His His His His His<br>    675 | 2037 |

<210> SEQ ID NO 2
<211> LENGTH: 678
<212> TYPE: PRT
<213> ORGANISM: Moloney murine sarcoma virus

<400> SEQUENCE: 2

Met Thr Leu Asn Ile Glu Asp Glu Tyr Arg Leu His Glu Thr Ser Lys
1     5     10     15

Glu Pro Asp Val Ser Leu Gly Ser Thr Trp Leu Ser Asp Phe Pro Gln
    20     25     30

Ala Trp Ala Glu Thr Gly Gly Met Gly Leu Ala Val Arg Gln Ala Pro
  35     40     45

Leu Ile Ile Pro Leu Lys Ala Thr Ser Thr Pro Val Ser Ile Lys Gln
50     55     60

Tyr Pro Met Ser Gln Glu Ala Arg Leu Gly Ile Lys Pro His Ile Gln
65     70     75     80

Arg Leu Leu Asp Gln Gly Ile Leu Val Pro Cys Gln Ser Pro Trp Asn
     85     90     95

Thr Pro Leu Leu Pro Val Lys Lys Pro Gly Thr Asn Asp Tyr Arg Pro
    100     105     110

Val Gln Asp Leu Arg Glu Val Asn Lys Arg Val Glu Asp Ile His Pro
  115     120     125

Thr Val Pro Asn Pro Tyr Asn Leu Leu Ser Gly Leu Pro Pro Ser His
130     135     140

Gln Trp Tyr Thr Val Leu Asp Leu Lys Asp Ala Tyr Phe Cys Leu Arg
145     150     155     160

Leu His Pro Thr Ser Gln Pro Leu Phe Ala Phe Glu Trp Arg Asp Pro

```
            165                 170                 175
Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
            195                 200                 205

Ala Asp Phe Arg Ile Gln His Pro Asp Leu Ile Leu Leu Gln Tyr Val
            210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
            245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
            275                 280                 285

Val Met Gly Gln Pro Thr Pro Lys Thr Pro Arg Gln Leu Arg Glu Phe
            290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
            325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
            355                 360                 365

Leu Phe Val Asp Glu Lys Gln Gly Tyr Ala Lys Gly Val Leu Thr Gln
            370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
            405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
            435                 440                 445

Pro Asp Arg Trp Leu Ser Asn Ala Arg Met Thr His Tyr Gln Ala Leu
            450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
            485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
            515                 520                 525

Leu Leu Gln Glu Gly Gln Arg Lys Ala Gly Ala Ala Val Thr Thr Glu
            530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
            565                 570                 575

Lys Lys Leu Asn Val Tyr Thr Asp Ser Arg Tyr Ala Phe Ala Thr Ala
            580                 585                 590
```

```
His Ile His Gly Glu Ile Tyr Arg Arg Gly Leu Leu Thr Ser Glu
        595                 600                 605

Gly Lys Glu Ile Lys Asn Lys Asp Glu Ile Leu Ala Leu Leu Lys Ala
610                 615                 620

Leu Phe Leu Pro Lys Arg Leu Ser Ile Ile His Cys Pro Gly Gly Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
        660                 665                 670

His His His His His His
        675

<210> SEQ ID NO 3
<211> LENGTH: 44
<212> TYPE: DNA
<213> ORGANISM: Artificial
<220> FEATURE:
<223> OTHER INFORMATION: oligonucleotide primer

<400> SEQUENCE: 3
cttagcataa tccattgtcc cgggggtcaa agggacaca gcgc                    44

<210> SEQ ID NO 4
<211> LENGTH: 44
<212> TYPE: DNA
<213> ORGANISM: Artificial
<220> FEATURE:
<223> OTHER INFORMATION: oligonucleotide primer

<400> SEQUENCE: 4
gcgctgtgtc cctttttgacc cccgggacaa tggattatgc taag                  44

<210> SEQ ID NO 5
<211> LENGTH: 47
<212> TYPE: DNA
<213> ORGANISM: Artificial
<220> FEATURE:
<223> OTHER INFORMATION: oligonucleotide primer

<400> SEQUENCE: 5
gaagctaaat gtttatactg attcccgggc tgcttttgct actgccc                47

<210> SEQ ID NO 6
<211> LENGTH: 47
<212> TYPE: DNA
<213> ORGANISM: artificial
<220> FEATURE:
<223> OTHER INFORMATION: oligonucleotide sequence

<400> SEQUENCE: 6
gggcagtagc aaaagcagcc cgggaatcag tataaacatt tagcttc                47

<210> SEQ ID NO 7
<211> LENGTH: 33
<212> TYPE: DNA
<213> ORGANISM: Artificial
<220> FEATURE:
<223> OTHER INFORMATION: oligonucleotide sequence

<400> SEQUENCE: 7
ggcaaccgga tggctaacca agcggcccga aag                               33
```

<210> SEQ ID NO 8
<211> LENGTH: 33
<212> TYPE: DNA
<213> ORGANISM: Artificial
<220> FEATURE:
<223> OTHER INFORMATION: oligonucleotide primer

<400> SEQUENCE: 8
ctttcgggcc gcttggttag ccatccggtt gcc                              33

<210> SEQ ID NO 9
<211> LENGTH: 34
<212> TYPE: DNA
<213> ORGANISM: Artificial
<220> FEATURE:
<223> OTHER INFORMATION: oligonucleitide primer

<400> SEQUENCE: 9
cacacctggt acacggaagg aagcagtctc ttac                             34

<210> SEQ ID NO 10
<211> LENGTH: 34
<212> TYPE: DNA
<213> ORGANISM: Artificial
<220> FEATURE:
<223> OTHER INFORMATION: oligonucleotide primer

<400> SEQUENCE: 10
gtaagagact gcttccttcc gtgtaccagg tgtg                             34

<210> SEQ ID NO 11
<211> LENGTH: 34
<212> TYPE: DNA
<213> ORGANISM: Artificial
<220> FEATURE:
<223> OTHER INFORMATION: oligonucleotide primer

<400> SEQUENCE: 11
cacacctggt acacgaatgg aagcagtctc ttac                             34

<210> SEQ ID NO 12
<211> LENGTH: 34
<212> TYPE: DNA
<213> ORGANISM: Artificial
<220> FEATURE:
<223> OTHER INFORMATION: oligonucleotide primer

<400> SEQUENCE: 12
gtaagagact gcttccattc gtgtaccagg tgtg                             34

<210> SEQ ID NO 13
<211> LENGTH: 32
<212> TYPE: DNA
<213> ORGANISM: artificial
<220> FEATURE:
<223> OTHER INFORMATION: oligonucleotide primer

<400> SEQUENCE: 13
cgctcagcgg gctgatctga tagcactcac cc                               32

<210> SEQ ID NO 14
<211> LENGTH: 32
<212> TYPE: DNA
<213> ORGANISM: artificial
<220> FEATURE:
<223> OTHER INFORMATION: oligonucleotide primer

```
<400> SEQUENCE: 14
gggtgagtgc tatcagatca gcccgctgag cg                                    32

<210> SEQ ID NO 15
<211> LENGTH: 33
<212> TYPE: DNA
<213> ORGANISM: Artificial
<220> FEATURE:
<223> OTHER INFORMATION: oligonucleotide primer

<400> SEQUENCE: 15
gatttaaagg atgcctattt ctgcctgaga ctc                                   33

<210> SEQ ID NO 16
<211> LENGTH: 33
<212> TYPE: DNA
<213> ORGANISM: Artificial
<220> FEATURE:
<223> OTHER INFORMATION: oligonucleotide primer

<400> SEQUENCE: 16
gagtctcagg cagaaatagg catcctttaa atc                                   33

<210> SEQ ID NO 17
<211> LENGTH: 36
<212> TYPE: DNA
<213> ORGANISM: artificial
<220> FEATURE:
<223> OTHER INFORMATION: oligonucleotide primer

<400> SEQUENCE: 17
gacccctcga caactactgg agttcctagg gacggc                                36

<210> SEQ ID NO 18
<211> LENGTH: 36
<212> TYPE: DNA
<213> ORGANISM: artificial
<220> FEATURE:
<223> OTHER INFORMATION: oligonucleotide primer

<400> SEQUENCE: 18
gccgtcccta ggaactccag tagttgtcga ggggtc                                36

<210> SEQ ID NO 19
<211> LENGTH: 39
<212> TYPE: DNA
<213> ORGANISM: artificial
<220> FEATURE:
<223> OTHER INFORMATION: oligonucleotide primer

<400> SEQUENCE: 19
tcctagggac ggcaggcgcc tgtcgcctct ggatccctg                             39

<210> SEQ ID NO 20
<211> LENGTH: 39
<212> TYPE: DNA
<213> ORGANISM: artificial
<220> FEATURE:
<223> OTHER INFORMATION: oligonucleotide primer

<400> SEQUENCE: 20
cagggatcca gaggcgacag gcgcctgccg tccctagga                             39
```

RECOMBINANT REVERSE TRANSCRIPTASES

CROSS-REFERENCE TO RELATED APPLICATIONS

This application is a continuation of U.S. application Ser. No. 12/568,364 filed Sep. 28, 2009 (now U.S. Pat. No. 8,361, 754), which is a continuation of U.S. application Ser. No. 10/827,498 filed Apr. 19, 2004 (now U.S. Pat. No. 7,595,179), which disclosures are herein incorporated by reference in their entirety.

TECHNICAL FIELD OF THE INVENTION

The present invention relates to recombinant Reverse Transcriptase (RT) enzymes with modified activity, and more particularly, to selectively mutated RTs with enhanced RNA directed, DNA polymerase activity that produce longer cDNAs, higher aRNA yields.

BACKGROUND OF THE INVENTION

Without limiting the scope of the invention, its background is described in connection with the use of RT enzymes for use in a wide variety of assays used by molecular biologists, as an example.

Heretofore, in this field, the RNA directed, DNA polymerase activity responsible for the synthesis of complementary DNA (cDNA) from an RNA template has been accomplished using reverse transcriptase enzymes, whether purified or recombinant. One such use for RTs if for transcription-based amplification systems, e.g., amplifying RNA and DNA target sequences.

Transcription-based amplification methods find use in a wide variety of settings, e.g., routine clinical laboratory use in diagnostic tests such as direct detection of pathogens. Another such use for RTs is in the initial step for RT-PCR (polymerase chain reaction) used to amplify an RNA target for analysis and/or cloning. In RT-PCR, the RT is used to make an initial complementary DNA (cDNA) copy of the RNA target, which is then amplified by successive rounds of DNA replication.

RTs have three primary enzymatic activities: a RNA-directed, DNA polymerase activity; a DNA-directed, DNA polymerase activity; and an RNase H activity. The RNase H activity degrades specifically RNA found in an RNA:DNA duplex. An initial goal of many molecular biologists was to identify an RT that had no detectable RNase H activity while still maintaining DNA polymerase activity. An RT having no RNase H activity would finds particular use because degradation of the RNA strand of RNA:DNA intermediates by RNase H causes unwanted degradation of the template reducing cDNA yields. U.S. Pat. Nos. 5,244,797, 5,540,776, 5,668, 005, 6,063,608, 6,589,768 and 6,610,522, disclose one such mutant RT, wherein a gross deletion mutant with no detectable RNase H activity is taught.

U.S. Pat. No. 5,998,195 teaches a method of reducing the level of RNase activity in an RT preparation by using an expression vector or plasmid containing a cloned version of the gene for an MMLV-RT which, when used to transform a suitable host cell such as E. coli, leads to the expression of the gene and the generation of a gene product having the DNA- and RNA-directed DNA polymerase activities and RNase H activity associated with retroviral reverse transcriptases. A host cell with a reduced level of ribonuclease activity as compared to wild-type strains is used to provide a source of RT that has endogenous levels of RNase activity below that of previous recombinant preparations.

Yet others have purified RT, e.g., Goff et al., U.S. Pat. No. 4,943,531 (1990) and Kotewicz et al., U.S. Pat. No. 5,017, 492, which have described methods for the purification of reverse transcriptase derived from Moloney Murine Leukemia Virus (MMLV-RT) and expressed in *E. coli*. These expression constructs and isolation and purification methods form the basis for the majority of commercial reverse transcriptase preparations.

SUMMARY OF THE INVENTION

The present invention relates to a gene that encodes a hyperactive reverse transcriptase having enhanced DNA polymerase activity. Increased DNA polymerase activity is achieved by one or more point mutations in the DNA processivity domain of the RT. Using the mutant RTs of the present invention greatly enhanced yields of aRNA may be achieved from template amounts in picogram amounts. In addition to enhanced amplification, the hyperactive RTs were found to consistently produce extra-long cDNAs, that is, messages exceeding 9 kb.

The present invention may also include one or more mutations to the nucleotide selection domain, which is located near the amino terminus of the RT. The present invention may also include one or more mutations in the processivity domain, which facilitates the formation of longer cDNA products. Mutants in the processivity domain of RT also exhibit substantially reduced RNase H activity (e.g., between about 0.1, 0.5, 1.0, 2.5, 5.0, 10 to about 50% percent of the wild-type activity of MMLV RT). The hyperactive mutants described herein are able to produce, enhanced amplification of mRNA to cDNA from very small quantities of template in both single and double rounds of amplification while maintaining message ratio fidelity.

More particularly, the present invention includes an isolated hyperactive reverse transcriptase that includes one or more point mutations in the processivity domain and/or one or more point mutations in the nucleotide selection domain. The reverse transcriptase may be, e.g., an AMV, M-MLV, HTLV-1, BLV, RSV, HFV, R2 *Bombyx mori* or HIV reverse transcriptase. The hyperactive reverse transcriptase is encoded by a modified nucleotide sequence that encodes a modified amino acid sequence modified in the processivity domain generally correspond with amino acids 497 to 671 of M-MLV reverse transcriptase. The modifications to the nucleotide selection domain may correspond to amino acids 153 to 158 of M-MLV reverse transcriptase. As disclosed herein, the reverse transcriptase may be used in the preparation of full-length cDNA and may be a hyperactive reverse transcriptase that is produced recombinantly and purified to, e.g., greater than about 90% pure.

Examples of mutations that have been developed and that show an increase in activity over the wild-type enzyme, as described and characterized herein include, e.g., mutations in the processivity domain with one or more of the following mutations corresponding to the amino acids in MMLV-RT: H638G, Y586A, D653N, D524N, D524E and E562D. For mutations in the nucleotide selection domain these may include one or more of the following mutations corresponding to the amino acids in MMLV-RT: F155, D153, A154, F155, F156, C157, or L158. In one group of specific examples that demonstrate the structure and functional relationship between the mutations, the mutation in the processivity domain may include one or more of the following mutations corresponding to the amino acids in MMLV-RT: H638G, Y586A, D653N, D524N, D524E and E562D and the mutation in the nucleotide selection domain may include one or more of the following mutations corresponding to the amino acids in MMLV-RT: F155Y. The hyperactive reverse transcriptase produces a yield of greater than about 1, 5, 7, 10, 15 or about 25 ug of an aRNA from 100 ng of template RNA in a single amplification reaction. Alternatively, the hyperactive reverse transcriptase produces a yield of greater than about 1, 2, 5 or even 10 ug of an aRNA from 10 pg of template RNA after a two-round amplification reaction. The hyperactive reverse transcriptase may produces a cDNA greater than about 6, 9 or even 11 or from between about 6 to about 15 kilobases, or greater than 15 kilobases in a single cDNA synthesis reaction. The hyperactive reverse transcriptase has a DNA polymerase activity of greater than about 200 Units per microgram, e.g., between about 0.1 and 300 Units per microgram. Generally, the reverse transcriptase of the present invention has an RNase H activity of between about 0.1 and about 25 percent of the wild-type RNase H activity of reverse transcriptases.

The present invention also includes an isolated reverse transcriptase having substantially reduced RNase H activity that one or more point mutations in the processivity domain. The RNase I activity of the reverse transcriptase has between about 0.1 and 50% of wild-type activity or between about 1 and 10% of wild-type RNase H activity of a wild-type reverse transcriptase, e.g., an MMLV-RT. The mutation in the processivity domain may include one or more of the following mutations corresponding to the amino acids in MMLV-RT: H638G, Y586A, D653N, D524N, D524E and E562D and may further include a mutation in the nucleotide selection domain comprises a mutation of residue F155 in MMLV-RT. The reverse trancriptase may be isolated and purified and include one or more mutations in the processivity domain corresponding to the amino acids in MMLV-RT: H638G, Y586A, D653N, D524N, D524E and E562D and a mutation in the nucleotide selection domain at F155Y.

Yet another embodiment of the present invention is an isolated protein having DNA polymerase activity and substantially reduced RNase H activity comprising one or more mutations in the processivity domain and one or more mutations in the nucleotide selection domain. The isolated protein having DNA polymerase activity and substantially reduced RNase H activity may produces a yield of greater than about 1, 5, 7, 10, 12, 15, 25 ug of an aRNA from 100 ng of template RNA in a single amplification reaction. Another method for characterizing the activity of the reverse transcriptase enzyme mutants disclosed herein is that the reverse transcriptase protein produces an aRNA yield of greater than about 20% as compared to an equivalent wild-type Reverse Transcriptase enzyme. Another characteristic is that the reverse transcriptase protein produces a yield of greater than about 1, 5 or 10 ug of an aRNA from 10 pg of template RNA after a two-round amplification reaction; a cDNA greater than about 6, 9 or even 11 kilobases in a single cDNA synthesis reaction; a cDNA greater than about 6 to about 15 kilobases in a single cDNA synthesis reaction or even a cDNA greater than about 15 kilobases in a single cDNA synthesis reaction. Generally, the DNA polymerase activity is greater than about 200 Units per microgram, e.g., between about 0.1 and 300 Units per microgram. Functionally, the mutant reverse transcriptase will have between about 0.1 and about 25 percent of the wild-type RNase H activity.

The present invention also includes an isolated and purified reverse transcriptase protein comprising one or more mutations in the nucleotide selection domain and may be selected from, e.g., AMV, M-MLV, HTLV-1, BLV, RSV, HFV, R2 *Bombyx mori* and/or HIV reverse transcriptase. The reverse transcriptase may also be modified at the nucleotide sequence to encodes a modified amino acid sequence in the processivity domain corresponding to amino acids 497 to 671 of M-MLV reverse transcriptase. When the nucleotide selection domain is mutated this may be one or more point mutations in the nucleotide selection domain corresponding to amino acids 153 to 158 of M-MLV reverse transcriptase and may be used in the preparation of full-length cDNA.

A process for making a protein with hyperactive reverse transcriptase activity may include the steps of: transforming a host cell with the hyperactive RT comprising a mutation in the processivity domain that comprises one or more of the following mutations corresponding to the amino acids in MMLV-RT: H638G, Y586A, D653N, D524N, D524E and E562D and further comprising a F155Y mutation in the nucleotide selection domain of MMLV-RT and culturing the host cell under conditions such that the hyperactive reverse transcriptase is produced by the host cell.

The present invention also includes an isolated and purified nucleic acid encoding a hyperactive reverse transcriptase with a mutation in the processivity domain and/or in the nucleotide selection domain. For example, the nucleic acid sequence may be modified to encode a hyperactive reverse transcriptase having a mutation that corresponds to and includes, e.g., an H638G mutation of the MMLV-RT, an F155Y mutation or an F155Y mutation and an H638G mutation. The nucleic acid has SEQ ID No.: 1 and further include, e.g., a nucleic acid segment encoding a leader sequence and/or encode a protein segment other than the hyperactive reverse transcriptase to form, e.g., a fusion protein. Another embodiment of the present invention is a vector that includes a nucleic acid having a nucleic acid encoding a hyperactive reverse transcriptase that encodes a mutation in the processivity domain and/or in the nucleotide selection domain.

Yet another embodiment of the present invention is a host cell transformed with an expression vector having a nucleic acid encoding an amino acid of SEQ ID NO.: 2, for a hyperactive reverse transcriptase. The host cell may be a bacteria, fungi, plant, or even a mammalian cell. One example of a host is *E. coli* or even *P. pastoris*. The host cell may even be transformed to express a hyperactive reverse transcriptase. The host cell, vector and constructs disclosed herein may be used in a process for making an isolated hyperactive reverse transcriptase that includes the steps of transforming a host cell with an isolated nucleic acid that encodes a hyperactive reverse transcriptase; and culturing the host cell under conditions such that the hyperactive reverse transcriptase is produced.

The hyperactive reverse transcriptase may include one or more mutations replace at least one of the amino acids of the processivity domain and the nucleotide selection domain, with an alternative naturally occurring L-amino acid, the replacement being selected from the group consisting of: (1) a substitution of any of isoleucine, valine, and leucine for any other of these amino acids; (2) a substitution of aspartic acid for glutamic acid or vice versa; (3) a substitution of glutamine for asparagine or vice versa; (4) a substitution of serine for threonine or vice versa; (5) a substitution of glycine for alanine or vice versa; (6) a substitution of alanine for valine or vice versa; (7) a substitution of methionine for any of leucine, isoleucine, or valine and vice versa; and (8) a substitution of lysine for arginine or vice versa. Alternatively, the replacement may be selected from the group consisting of: (1) a substitution of any of isoleucine, valine, or leucine for any other of these amino acids; (2) a substitution of aspartic acid for glutamic acid or vice versa; (3) a substitution of glutamine for asparagine or vice versa; and (4) a substitution of serine for threonine or vice versa and wherein the hyperactive reverse transcriptase comprises a hyperactive reverse transcriptase.

The present invention also includes a variety of kits that use the present invention, which will generally include instructions for the use of the hyperactive reverse transcriptase and a variety of buffers, controls and the like. One example of a kit may be used to synthesize nucleic acid synthesis, and includes in a suitable container: a hyperactive reverse transcriptase; and a reaction solution for the reverse transcriptase. The kit may also include information insert may include information for using the reverse transcriptase, a reaction solution comprises a 10× concentrated reverse transcriptase reaction buffer, a primer, a reverse transcriptase buffer, a PCR buffer, a single contained with a mix of nucleotides or containers that each hold individual nucleotides, a buffer for in vitro transcription, a template purification column and/or one or more magnetic particles suitable for nucleic acid purification. Alternatively, the kit for nucleic acid synthesis, may include in a suitable container a hyperactive reverse transcriptase comprising one point mutation in the processivity domain; and a reaction solution for the reverse transcriptase. Another kit may includes suitable containers having a hyperactive reverse transcriptase comprising one point mutation in the processivity domain and one point mutation in the nucleotide selection domain; and a reaction solution for the reverse transcriptase.

The present invention also includes a method for RNA amplification that includes the steps of, reverse transcribing an RNA template into a single-stranded cDNA with a hyperactive reverse transcriptase in the presence of an oligonucleotide comprising a transcriptional promoter and a primer, purifying the single-stranded cDNA; and generating amplified RNA (aRNA) using an RNA polymerase. Alternatively, a method for RNA amplification may includes the steps of: reverse transcribing an RNA template into a single-stranded cDNA with a hyperactive reverse transcriptase in the presence of an oligonucleotide comprising a transcriptional promoter and a primer, converting the single-stranded cDNA into double-stranded cDNA using a DNA polymerase, purifying the double-stranded cDNA and generating amplified RNA (aRNA) using an RNA polymerase. The method may also include purifying the aRNA and aRNA made using the methods disclosed herein.

Yet another kit may be for RNA amplification and includes in one or more suitable containers a hyperactive reverse transcriptase that includes one or more point mutations in the processivity domain and one or more point mutations in the nucleotide selection domain; an oligonucleotide with a transcriptional promoter region and/or oligo(dT) region; a DNA polymerase; and an RNA polymerase. The kit may also includes one or more of the following: an insert may be provided that includes information for using the optimized reverse transcriptase, a 10× concentrated reverse transcriptase reaction buffer, a primer, a reverse transcriptase buffer, a DNA Polymerase buffer, a mix of nucleotides, separate containers for individual nucleotides, a buffer for in vitro transcription, a nucleic acid purification column and/or a magnetic particle or particles suitable for nucleic acid purification.

Another kit for RNA amplification may include one or more suitable containers that include: a hyperactive reverse transcriptase with one or more point mutations in the processivity domain; an oligonucleotide with a transcriptional promoter region and oligo(dT) region; a DNA polymerase; and an RNA polymerase. The kits, methods and compositions disclosed herein may be used to make an aRNA including a ssDNA or a DNA:RNA hybrid made from an RNA template by a hyperactive reverse transcriptase. Also included may be an RT-PCR kit with one or more suitable containers: a hyperactive reverse transcriptase, two or more primers, nucleotides, a thermostable DNA polymerase and an RT-PCT buffer. The same container or a separate container may also be provided that includes one or more reverse transcriptases in addition to the hyperactive reverse transcriptase of the present invention as a control or to provide additional reverse transcriptase activity.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 1 shows the domain structure of MMLV RT, point mutations relevant herein are marked;

FIG. 2 shows the gene sequence of F155Y;H638G MMLV RT (SEQ ID NO: 1);

FIG. 3 shows the protein sequence of F155Y;H638G MMLV RT (SEQ ID NO: 2), wherein amino acid number 1 of SEQ ID NO: 2 is the threonine following the initial methionine;

FIG. 4 is a gel that shows a comparison of cDNA Product Lengths by Various Mutant MMLV RT Enzymes using RNA Templates from 0.5 to 9.0 kb in Size;

DETAILED DESCRIPTION OF THE INVENTION

Figure 5:
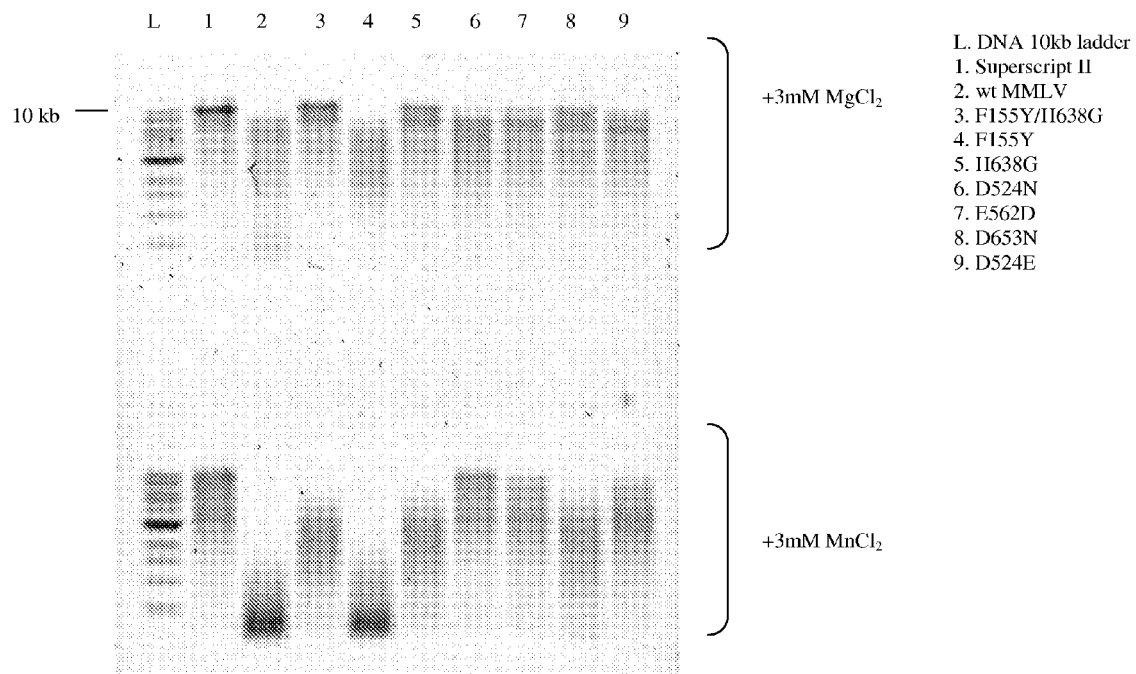
FIG. 5 is a gel of the cDNA synthesis products using a 9 kb RNA template with MMLV RT mutants in the presence of $MgCl_2$ or $MnCl_2$.

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention and do not delimit the scope of the invention.

DEFINITIONS

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims. As used throughout the present specification the following abbreviations are used: kb, kilobase (pairs); kD, kilodalton; PCR, polymerase chain reaction; RT, reverse transcriptase; MMLV, murine moloney leukemia virus; AMV, avian myoblastosis virus; RSV, Rous sarcoma virus; HIV, human immunodeficiency virus; HFV, human foamy virus.

The invention relates to the production of hyperactive RTs. The present invention also includes RTs having DNA polymerase activity and substantially reduced RNase H activity made using recombinant DNA techniques wherein the RT is modified using point mutations. More particularly, the present invention includes RTs with one or more point mutations in the nucleotide selection domain, RTs with one or more point mutations in the processivity domain, and hyperactive RTs that include RTs with mutations in both the nucleotide selection and the processivity domains. The RTs disclosed herein may be expressed in host cells using, e.g., recombinant plasmids constructed as described herein that provide reverse transcriptase for use in recombinant DNA technology to synthesize cDNA from mRNA without the unwanted effects of RNase H activity, which can excessively degrade the mRNA template during first-strand synthesis.

As used herein, the terms "hyperactive Reverse Transcriptase," "hyperactive RT" and the like are used to describe a hyperactive RT purified to near homogeneity and having the ability to enable greater than 20% more amplified RNA that can be generated by the polymerase activity of a wild-type RT DNA polsymerase domain from an input of 100 ng total RNA in an RNA amplification reaction that includes a 4 hr in vitro transcription reaction. For example, an isolated hyperactive Reverse Transcriptase that includes one or more point mutations in the "processivity domain" and one or more point mutations in the "nucleotide selection domain" is able to generate a yield of greater than 5 micrograms of aRNA in a single amplification reaction from 100 ng of total RNA, e.g., in a single round RNA amplification of 100 ng HeLa S-3 Total RNA or Rat Thymus Total RNA against wild-type enzyme MMLV-RT, AMV RT or any other RT as determined by, e.g., UV absorbance at 260 nm or other equivalent methods known to the skilled artisan. As will be apparent to those of skill in the art, the "hyperactivity" of the enzymes of the present invention may be as quantitatively distinct due to, e.g., assay conditions, temperatures, times, salts, source of RNA, quality of RNA, activity read-out and the like.

The term "processivity domain" is used to describe the region of the RT that is responsible for maintenance of the template integrity in a standard RT reaction. As defined herein, the processivity domain includes amino acids 497-671. One indication of processivity is the average length of the cDNA that can be synthesized from a long mRNA target.

The present invention is distinct from the domains identified by, e.g., Gerard, et al., U.S. Pat. No. 5,668,005 and patents related thereto, which functionally identified the region spanning MMLV RT amino acids 503 through 611 as critical for RNase H activity. In contrast to the region identified by Gerard, et al., the present invention identifies locations and mutations outside of this previously characterized region as also affect RNase H activity and, importantly, enzyme processivity. Indeed, the mutant RT enzymes described herein catalyze yields of amplified RNA that are superior to other, commercially available enzymes mutated in the RNase H domain, such as SuperScript II. As a result, the inventors describe novel mutations that enable a large and unexpected improvement in the yield of amplified RNA in Eberwine-like RNA amplification protocols. The hyperactive RT with mutations in the processivity domain of the RTs may also include one or more point mutations in other domains. The present inventors have identified one series of mutants that can affect the sensitivity of the RT for distinguishing or having a preference for ribonucleotides and/or deoxyribonucleotides during DNA synthesis, which are described herein as the "nucleotide selection domain." As used herein the phrase "nucleotide selection domain" or "NSD" includes but is not limited to, mutations in the following amino acids in MMLV-RT: D153, A154, F155, F156, C157, or L158 and the equivalent mutations in other RTs. The equivalent mutation in the other RTs may be localized based on the crystal structure of MMLV RT, which reveals a secondary structure motif that encompasses a $3_{10}$ helix around the nucleotide selection domain namely, amino acids 153 to 158 of the MMLV-RT.

Described herein are point mutations that alone or in combination significantly enhance the yield of amplified nucleic acids used useful for, e.g., the amplification of isolated RNA for use in nucleic acid microarrays. Another method to detect the activity of the hyperactive RTs of the present invention is the length of the cDNAs, wherein the hyperactive RTs are able to copy an mRNA to a product length greater than 9, 11, 15 or even 20 kilobases.

As used herein, the term "substantially reduced RNase H activity" is used to describe an RT purified to near homogeneity and having an RNase H activity of between about 0.01%, 1, 3, 4, 6, 9, 10, 15, 20, 25 and 50% of the RNase H activity of a wild-type RT RNase H domain. Described herein are point mutations that alone or in combination reduce the level of degradation of the RNA template used in an RT reaction, that is, without significant degradation of the mRNA template during first-strand synthesis, but that maintain "processive" activity. The term "processivity" as used herein is used to describe the ability of the RT to elongate its nucleic acid product to produce a longer product. This processivity domain includes, but is not limited to, one or more of the following mutations corresponding to the amino acids in MMLV-RT: H638G, Y586A, D653N, D524N, D524E and E562D. The double mutants of the present invention also include mutations to the processivity domain corresponding to the amino acids in MMLV-RT: H638G, Y586A, D653N, D524N, D524E and E562D and one or more mutations to the nucleotide selection domain that include one or more of the following mutations in the following amino acids in MMLV-RT: D153, A154, F155, F156, C157, or L158.

The term "degenerate variants" as used herein describes having variations in the DNA or amino acid sequence that vary the amino acids at the processivity domain and the nucleotide selection domain such that the activities described herein are maintained. The term "codon-optimized" sequence is used to describe a hyperactive RT in which at least a portion of the sequence has been modified by directed sequence modification, for example, changes to the sequence in one or more underlying sequences that may or may not affect the amino acid sequence but that are use to, e.g., improve the expression of the protein by using codons that are more commonly used in a particular host organism. By the term "recombinant," "isolated," "cloned" hyperactive RT or grammatical equivalents herein is meant a polypeptide having a modified nucleic or amino acid sequence of a mature RT (for example, from about 85 to 100% identical) as described herein, as well as amino acid sequence variants that are enzymatically active RNA directed, DNA polymerases with a catalytic profile that is distinct from that of wild type RT, e.g., AMV RT, MMLV RT and the like as defined hereinabove. In addition, sequences may be the combination of sequences from different organisms for the same or closely related sequences to, e.g., modify the functionality of the final protein by directed modifications or even to permit specific recombinant modification or manipulation by the user.

As defined herein, a "wild type" sequence, whether found in a coding, non-coding or interface sequence is an allelic form of sequence that performs the natural or normal function for that sequence. Therefore, as used herein a wild type sequence includes multiple allelic forms of a cognate sequence, for example, multiple alleles of a wild type sequence may encode silent or conservative changes to the protein sequence that a coding sequence encodes. A "mutant" sequence is defined herein as one in which at least a portion of the functionality of the sequence has been lost, for example, changes to the sequence in a promoter or enhancer region will affect at least partially the expression of a coding sequence in an organism. A "mutation" in a sequence as used herein is any change in a nucleic acid sequence that may arise such as from a deletion, addition, substitution, or rearrangement. The mutation may also affect one or more steps that the sequence is involved in. For example, a change in a DNA sequence may lead to the synthesis of an altered protein, one that is inactive, or to an inability to produce the protein. A "mutation frequency" as used herein is the frequency or rate with which a particular mutation appears in a particular dataset. Mutation frequency may also be the frequency at which any mutation appears in the whole dataset.

A sample is any mixture of macromolecules obtained from a solution, a cell culture, a supernatant, an animal, an environmental sample, a food sample or even a patient. This also includes separated fractions of all of the preceding. Examples of samples include, but are not limited to, blood, plasma, urine, semen, saliva, lymph fluid, meningeal fluid, amniotic fluid, glandular fluid, and cerebrospinal fluid. "Sample" also includes solutions or mixtures containing homogenized solid material, such as feces, cells, tissues, and biopsy samples. Samples herein include one or more that are obtained at any point in time, including diagnosis, prognosis, and periodic monitoring.

The terms "a sequence essentially as set forth in SEQ ID NO.: (#)", "a sequence similar to", "nucleotide sequence" and similar terms, with respect to nucleotides, refers to sequences that substantially correspond to any portion of the sequence identified herein as SEQ ID NO.: 1 or the point mutants and combination of point mutants of RTs described herein and the functional counterparts in related RTs. These terms refer to synthetic as well as naturally-derived molecules and includes sequences that possess biologically, immunologically, experimentally, or otherwise functionally equivalent activity, for instance with respect to hybridization by nucleic acid segments, or the ability to encode all or portions of an RT having DNA polymerase and/or substantially reduced RNase H activity. Naturally, these terms are meant to include information in such a sequence as specified by its linear order.

The term "homology" refers to the extent to which two nucleic acids are complementary. There may be partial or complete homology. A partially complementary sequence is one that at least partially inhibits a completely complementary sequence from hybridizing to a target nucleic acid and is referred to using the functional term "substantially homologous." The degree or extent of hybridization may be examined using a hybridization or other assay (such as a competitive PCR assay) and is meant, as will be known to those of skill in the art, to include specific interaction even at low stringency.

The inhibition of hybridization of the completely complementary sequence to the target sequence may also be examined using a hybridization assay involving a solid support (e.g., Southern or Northern blot, solution hybridization and the like) under conditions of low stringency. Low stringency conditions may be used to identify the binding of two sequences to one another while still being specific (i.e., selective). The absence of non-specific binding may be tested by the use of a second target that lacks even a partial degree of complementarity (e.g., less than about 30% identity). In the absence of non-specific binding, the probe will not hybridize to the second non-complementary target and the original interaction will be found to be selective. Low stringency conditions are generally conditions equivalent to binding or hybridization at 42 degrees Centigrade in a solution consisting of 5×SSPE (43.8 g/l NaCl, 6.9 g/l $NaH_2PO_4$—$H_2O$ and 1.85 g/l EDTA, pH 7.4), 0.1% SDS, 5×Denhardt's reagent (50×Denhardt's contains per 500 ml: 5 g Ficoll (Type 400, Pharmacia), 5 g BSA (Fraction V; Sigma) and 100 micrograms/ml denatured salmon sperm DNA); followed by washing in a solution comprising 5×SSPE, 0.1% SDS at 42 degrees Centigrade when a probe of about 500 nucleotides in length is employed. The art knows that numerous equivalent conditions may be employed to achieve low stringency conditions. Factors that affect the level of stringency include: the length and nature (DNA, RNA, base composition) of the probe and nature of the target (DNA, RNA, base composition, present in solution or immobilized, etc.) and the concentration of the salts and other components (e.g., formamide, dextran sulfate, polyethylene glycol). Likewise, the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, inclusion of formamide, etc.).

The term "gene" is used to refer to a functional protein, polypeptide or peptide-encoding unit. As will be understood by those in the art, this functional term includes genomic sequences, cDNA sequences, or fragments or combinations thereof, as well as gene products, including those that may have been altered by the hand of man. Purified genes, nucleic acids, protein and the like are used to refer to these entities when identified and separated from at least one contaminating nucleic acid or protein with which it is ordinarily associated. As used herein the terms "protein", "polypeptide" or "peptide" refer to compounds comprising amino acids joined via peptide bonds and are used interchangeably.

As used herein, the term "vector" is used in reference to nucleic acid molecules that transfer DNA segment(s) from one cell to another. The vector may be further defined as one designed to propagate specific sequences, or as an expression vector that includes a promoter operatively linked to the specific sequence, or one designed to cause such a promoter to be introduced. The vector may exist in a state independent of the host cell chromosome, or may be integrated into the host cell chromosome The term "host cell" refers to cells that have been engineered to contain nucleic acid segments or altered segments, whether archeal, prokaryotic, or eukaryotic. Thus, engineered, or recombinant cells, are distinguishable from naturally occurring cells that do not contain genes introduced recombinantly through the hand of man.

The term "altered", or "alterations" or "modified" with reference to nucleic acid or polypeptide sequences is meant to include changes such as gross or point: insertions, deletions, substitutions, fusions with related or unrelated sequences, such as might occur by the hand of man, or those that may occur naturally such as polymorphisms, alleles and other structural types. Alterations encompass genomic DNA and RNA sequences that may differ with respect to their hybridization properties using a given hybridization probe. Alterations of polynucleotide sequences for a hyperactive reverse transcriptase, or fragments thereof, include those that increase, decrease, or have no effect on functionality. Alterations of polypeptides refer to those that have been changed by recombinant DNA engineering, chemical, or biochemical modifications, such as amino acid derivatives or conjugates, or post-translational modifications.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it effects the transcription of the sequence; or a ribosome binding site is operably linked to e coding sequence if it is positioned so as to facilitate translation. Generally, "operably linked" means that the DNA sequences being linked are contiguous and, in the case of a secretory leader, contiguous and in same reading frame. Enhancers do not have to be contiguous Linking is accomplished by ligation at convenient restriction sites. If such sites do not exist, then synthetic oligonucleotide adaptors or linkers are used in accord with conventional practice.

As used herein, the expressions "cell" and "cell culture" are used interchangeably end all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Different designations are will be clear from the contextually clear.

"Plasmids" are designated by, e.g., a lower case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Transformation," as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome.

As used herein, the term "vector" is used in reference to nucleic acid molecules that transfer DNA segment(s) from one cell to another. The term "vehicle" is sometimes used interchangeably with "vector." The term "vector" as used herein also includes expression vectors in reference to a recombinant DNA molecule containing a desired coding sequence and appropriate nucleic acid sequences necessary for the expression of the operably-linked coding sequence in a particular host organism. Nucleic acid sequences necessary for expression in prokaryotes usually include a promoter, an operator (optional), and a ribosome binding site, often along with other sequences. The choice of a suitable vector depends on a number of considerations known to one of ordinary skill in the art, such as the size of the fragment, nature of the host, number and position of restriction sites desired, and the selection of marker and markers desired for selection. Expression of the RT genes may also be placed under control of other regulatory sequences homologous or heterologous to the host organism in its untransformed state as will be known to the skilled artisan. The selection of the host cell for transformation may influence the decision of which vector and/or regulatory sequences are provided along with the RT construct. Eukaryotic cells are known to utilize promoters, enhancers, and termination and polyadenylation signals.

As used herein, the term "amplify", when used in reference to nucleic acids refers to the production of a large number of copies of a nucleic acid sequence by any method known in the art. Amplification is a special case of nucleic acid replication involving template specificity. Template specificity is frequently described in terms of "target" specificity. Target sequences are "targets" in the sense that they are sought to be sorted out from other nucleic acid. Amplification techniques have been designed primarily for this sorting out.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer may be single stranded for maximum efficiency in amplification but may alternatively be double stranded. If double stranded, the primer is first treated to separate its strands before being used to prepare extension products. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g. ELISA, as well as enzyme-based histochemical assays), fluorescent, radioactive, and luminescent systems. It is not intended that the present invention be limited to any particular detection system or label.

As used herein, the term "target" when used in reference to the polymerase chain reaction, refers to the region of nucleic acid bounded by the primers used for polymerase chain reaction. Thus, the "target" is sought to be sorted oat from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195, 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular the amplified segments created by the PCR process itself are, themselves, efficient templates for subsequent PCR amplifications.

The reverse transcriptase gene (or the genetic information contained therein) can be obtained from a number of different sources, e.g., Moloney Murine leukemia virus (M-MLV); human T-cell leukemia virus type I (HTLV-I); bovine leukemia virus (BLV); Rous Sarcoma Virus (RSV); human immunodeficiency virus (HIV); yeast, including *Saccharomyces, Neurospora, Drosophila*; primates; and rodents. See, e.g., Weiss et al., U.S. Pat. No. 4,663,290 (1987); Gerard, G. R., DNA 5:271-279 (1986); Kotewicz, M. L., et al., Gene 25:249-258 (1985); Tanese, N., et al., Proc. Natl. Acad. Sci. (USA) 82:4944-4948 (1985); Roth, M. J., et al., J. Biol. Chem. 260:9326-9335 (1985); Michel, F., et al., Nature 316:641-643 (1985); Akins, R. A., et al., Cell 47:505-516 (1986), EMBO J. 4:1267-1275 (1985); and Fawcett, D. F., Cell 47:1007-1015 (1986). For instance, the gene may be obtained from public sources, e.g., ATCC, or may even be purified from eukaryotic cells infected with a retrovirus, or from a plasmid that includes a portion the retrovirus genome that includes the RT.

The mutation(s) for producing a hyperactive polymerase domain as described herein may be obtained by point mutation(s) in the processivity domain as described and disclosed herein. Likewise, RT genes having DNA polymerase activity and substantially reduced RNase H activity may be obtained by point mutation(s) of the nucleotide selection domain. The plasmid thus obtained may then be used to transform hosts which may then be screened for hyperactive RT activity. RT RNase H activity may also be assayed by template solubilization as compared to, e.g., a wild-type AMV, MMLV or other RT.

The invention also includes fusion proteins that include the hyperactive reverse transcriptase of the invention with, e.g., a carrier protein or other anchor domain that permits isolation and purification. It is also possible to prepare fusion proteins of the hyperactive reverse transcriptase that are substituted at the amino or carboxy termini with polypeptides which stabilize or change the solubility of the reverse transcriptase. Amino-terminal and carboxy-terminal gene fusion protein domains are well known in the art.

The transformed hosts of the invention may be cultured under, e.g., protein producing conditions according to any of the methods that are known to those skilled in the art or protein production, purification, isolation and characterization. Of particular use may be host cells that have reduced endogenous RNase activity, e.g., as taught in U.S. Pat. No. 5,998,195, relevant host cells, constructs, vectors and methods incorporated herein by reference. The hyperactive RT of the present invention may be isolated according to conventional methods known to those skilled in the art. For example, after protein expression the host cells may be collected by centrifugation, washed with suitable buffers, lysed, and the reverse transcriptase isolated by column chromatography, for example, on DEAE-cellulose, phosphocellulose or other standard isolation and identification techniques using, for example, polyribocytidylic acid-agarose, or hydroxylapatite or by electrophoresis or immunoprecipitation.

The hyperactive RT of the present invention may be used with any assay and included in any kit that calls for an RT, e.g., it may be used to prepare cDNA from RNA by hybridizing a primer, e.g., an oligo(dT) primer, or other complementary primers with the mRNA. The hyperactive RT of the present invention is particularly useful for the synthesis of full-length and/or extra-long length, complete cDNA by adding the hyperactive RT and all four deoxynucleoside triphosphates under conditions that permit elongation. Using the hyperactive RT produced by the present invention allows for the preparation of cDNA from mRNA with reduced degradation of the mRNA, which results in cDNA synthesis of messages exceeding 9, 12 or even 15 kilobases.

The hyperactive RT of the present invention is suited for incorporation into a kit for the preparation of cDNA from RNA, for aRNA synthesis and for amplification of mRNA for microarray analysis. Such a kit will generally include one or more containers, such as vials, tubes, and the like, and the kit will containers that have alone or in combination one or more of the separate elements of the method used, e.g., to prepare cDNA from RNA or for amplification of the RNA. For example, the kit may include one vial that has the hyperactive RT in solution. Separate containers may include suitable buffers, substrates for DNA synthesis such as the deoxynucleotides, oligo(dT) primer, and even a control RNA for use as a standard.

The reverse transcriptase may be present in the solution at a concentration of 5, 10, 100, 200, 400 or more units/ml. The reverse transcriptase may also be lyophilized in a plate well, and its activity reconstituted upon hydration of the lyophilized enzyme. Deoxynucleotides may be present either in lyophilized form, as part of a buffer or in solution at a concentration of, e.g., about 0.5 mM to about 2 mM each. A suitable buffer, present at 2, 5, 10, 50 and/or 100 times the final concentration of use may be, e.g., 250 mM Tris-HCl (pH 7.5 to 8.3), 375 mM KCl, 15 mM $MgCl_2$, and 50 mM dithiothreitol. An oligo (dT) may be present at a concentration of 5 ug/ml to 20 ug/ml. Control RNA, such as 2.3, 9.0 or greater kilobase control RNA, may be present at a concentration of 10 ug/ml to 20 ug/ml.

Reverse transcriptase-polymerase chain reaction (RT-PCR) and/or simultaneous DNA cleavage and reverse transcription may be conducted using the hyperactive RT. The hyperactive RT of the present invention may used in conjunction with standard RT-PCR techniques. RT-PCR is a common molecular biology procedure that typically requires DNA-free RNA. DNase I digestion of contaminating DNA is the method of choice for eradicating DNA in RNA preparations destined for reverse transcription and PCR.

EXAMPLE 1

The present inventors recognized that current RT mutants fail to provide the best combination of amplification, processivity, fidelity and ease of use. As such, the inventors focused on the creation of plasmids expressing H638G MMLV RT, Y586A MMLV RT, D653N MMLV RT, D524N MMLV RT, D524E MMLV RT, and E562D MMLV RT. Efforts to develop an improved RT for RNA amplification began with strategies for modulating RT-associated RNase H activity. MMLV and AMV-related RTs with no RNase H activity are known to synthesize longer cDNA products than their RNase $H^+$ counterparts. However, a complete loss of RNase H activity may have untoward effects in some applications (for an example, see Biotechniques 2002 June; 32(6): 1224-5). In fact, RNase H treatment of first strand cDNA is an obligate step in the aRNA synthesis procedure. Thus, an appropriately balanced ratio of RNase H to polymerase activity was potentially desirable.

As MMLV RT is modified easily by molecular techniques, this enzyme was the target for improvement efforts. FIG. 1 shows the relative domain structure of MMLV RT with the relevant point mutations of the present invention marked in relation to the domains. The present inventors identified a number of amino acid residues within the DNA polymerase domain and carboxy from the RNase H domain of MMLV RT as potential targets for site-directed mutagenesis. This domain is composed of a portion of the carboxy-terminus of the RT. For example, one group has identified amino acid residues 503-611 as critical for RNase H activity by gross deletion. Although the three dimensional structure of MMLV RT RNase H domain has not been solved, the corresponding structure of E. coli RNase H1 is known (Science. 1990 Sep. 21; 249(4975):1398-405). However, E. coli RNase H1 shares only 30% identity with the MMLV RNase H (Proc Natl Acad Sci USA. 1986 October; 83(20): 7648-52), which include essential metal binding and active site residues. Several "support" residues not directly involved in catalysis were also identical in the two enzymes. Several mutants of E. coli RNase H1 have been identified that exhibit reduced RNase H activity. The data provided herein support the choice of 9-10 mutants that were found to enhance the ability of the RT to maintain template interactions, significantly reduce the RNase H activity of MMLV RT to a level in the 1-50% range as compared to the wild-type MMLV RT, but not having the deleterious effects of deletion mutants or mutants having no RNase H activity. The results disclosed herein demonstrate that reduced activity (but not eliminated or no RNase H activity), is desirable for the aRNA synthesis application and the creation of a hyperactive RT.

The present inventors have developed a series of point mutants, e.g., H638G MMLV RT, Y586A MMLV RT, D653N MMLV RT, D524N MMLV RT, D524E MMLV RT, and E562D MMLV RT using pSE380 containing the MMLV RT gene (pSE380-MMLV RT) and the mutagenic primers given in Table 1. The nucleic acid sequence for one such mutant is shown in FIG. 2, with the amino acid sequence described in FIG. 3. Amplification of the mutant sequences was accomplished via PCR using the Quick Change mutagenesis kit (Stratagene). The resulting PCR product was transformed and plated onto solid media containing ampicillin Plasmid DNA from selected clones was prepared with the QIAprep Spin Miniprep Kit. In the case of Y586A MMLV RT and H638G MMLV RT, the presence of the correct mutation was diagnosed after restriction digest with Sma I. Clones containing D653N, D524N MMLV RT, D524E MMLV RT, and E562D MMLV RT were screened by sequencing. In each case, sequencing across the MMLV gene confirmed the desired mutations.

TABLE 1

Mutagenic Primers Used to Create H638G MMLV RT, Y586A MMLV RT, and D653N MMLV RT.

H638G-F
CTTAGCATAATCCATTGTCCCGGGGGTCAAAAGGGACACAGCGC
(SEQ ID NO.: 3);

H638G-R
GCGCTGTGTCCCTTTTGACCCCCGGGACAATGGATTATGCTAAG
(SEQ ID NO.: 4);

Y586A-F
GAAGCTAAATGTTTATACTGATTCCCGGGCTGCTTTTGCTACTGCCC
(SEQ ID NO.: 5);

Y586A-R
GGGCAGTAGCAAAAGCAGCCCGGGAATCAGTATAAACATTTAGCTTC
(SEQ ID NO.: 6);

D653N-F
GGCAACCGGATGGCTAACCAAGCGGCCCGAAAG (SEQ ID NO.: 7);

D653N-R
CTTTCGGGCCGCTTGGTTAGCCATCCGGTTGCC (SEQ ID NO.: 8);

D524E-F
CACACCTGGTACACGGAAGGAAGCAGTCTCTTAC (SEQ ID NO.: 9);

D524E-R
GTAAGAGACTGCTTCCTTCCGTGTACCAGGTGTG (SEQ ID NO.: 10);

D524N-F
CACACCTGGTACACGAATGGAAGCAGTCTCTTAC (SEQ ID NO.: 11);

D524N-R
GTAAGAGACTGCTTCCATTCGTGTACCAGGTGTG (SEQ ID NO.: 12);

E562D-F
CGCTCAGCGGGCTGATCTGATAGCACTCACCC (SEQ ID NO.: 13); and

E562D-R
GGGTGAGTGCTATCAGATCAGCCCGCTGAGCG (SEQ ID NO.: 14).

"F" and "R" refer to "forward" and "reverse" primers, respectively.

EXAMPLE 2

Creation of plasmids expressing F155Y MMLV RT, R301L MMLV RT, and F309A MMLV RT. Clones F155Y MMLV RT, R301L MMLV RT, and F309A MMLV RT were created using pSE380 containing the MMLV RT gene (pSE380-MMLV RT) and the mutagenic primers given in Table 2. Amplification of the mutant sequences was accomplished via PCR using the Quick Change mutagenesis kit (Stratagene). The resulting PCR product was transformed and plated onto solid media containing ampicillin Plasmid DNA from selected clones was prepared with the QIAprep Spin Miniprep Kit. For each mutant, sequencing across the MMLV gene confirmed the desired mutations.

TABLE 2

Mutagenic Primers Used to Create F155Y MMLV RT, R301L MMLV RT, and F309A MMLV RT.

F155Y-F
GATTTAAAGGATGCCTATTTCTGCCTGAGACTC (SEQ ID NO.: 15);

F155Y-R
GAGTCTCAGGCAGAAATAGGCATCCTTTAAATC (SEQ ID NO.: 16);

R301L-F
GACCCCTCGACAACTACTGGAGTTCCTAGGGACGGC (SEQ ID NO.: 17);

R301L-R
GCCGTCCCTAGGAACTCCAGTAGTTGTCGAGGGGTC (SEQ ID NO.: 18);

F309A-F
TCCTAGGGACGGCAGGCGCCTGTCGCCTCTGGATCCCTG (SEQ ID NO.: 19); and

F309A-R
CAGGGATCCAGAGGCGACAGGCGCCTGCCGTCCCTAGGA (SEQ ID NO.: 20).

"F" and "R" refer to "forward" and "reverse" primers, respectively.

EXAMPLE 3

Creation of Multiple Mutated MMLV RT Enzymes: Combined Polymerase and RNase H Mutations. To create combined MMLV RT mutants, plasmids containing the single mutations were used as templates for a second-round and/or third-round mutagenesis reaction. For example, to create the F155Y;H638G MMLV RT mutant, the following changes to the RT gene were made, beginning with wild-type MMLV RT (Accession number J02255):
1) Wild-type MMLV RT gene→Change F155 to Y155
2) F155Y MMLV RT→Change H638 to G638

EXAMPLE 4

Expression and Purification of MMLV RT Mutants. Plasmids carrying each mutated MMLV RT gene were transformed into XL-1 Blue E. coli cells. Single colonies were picked, and cultured overnight in LB media containing Ampicillin. The next day, 5 ml of the culture was used to inoculate 0.5-4 L of LB-Amp. Cells were grown to A600~0.4 at ~29° C. with 250 rpm shaking, and then induced with IPTG. After 12-16 hr growth at ~29° C., cell pellets were harvested for purification.

The MMLV mutants may be isolated and purified using a multitude of techniques known by the skilled artisan depending, e.g., in the level of purity desired and the expected uses of the MMLV. Examples of methods of purification include, e.g., crude filtration, column purification, epitope tagging, isolation by specific or non-specific binding to resins, selective secretion and the like. In one example, purification of the MMLV RT mutants was accomplished by resuspending frozen cells from cultures in a buffered, ionically controlled solution, e.g., a buffer containing 20 mM KPi pH 7.0, 500 mM NaCl and a protease inhibitor, e.g., 1 mM PMSF. The contents of the resuspended cells are then extracted using standard methods, e.g., French press, shearing or even lysozyme digestion 4 C for 30 min, followed by sonication or other forms of mechanical stress. The cell debry may then be cleared by centrifugation or filtration. Examples of well-known techniques for cellular content release such as cellular permeabilization are summarized in, e.g., U.S. Pat. No. 6,630,333, relevant portions incorporated herein by reference.

Following the release of the hyperactive reverse transcriptase enzymes of the present invention, whether alone or as fusion proteins, a variety of protein purification techniques may be followed that are well-known to one of ordinary skill in the art. Suitable techniques for purification include, but are not limited, e.g., ammonium sulfate and/or ethanol precipitation, acid extraction, preparative gel electrophoresis, immunoadsorption, anion or cation exchange chromatography, phosphocellulose chromatography, hydrophobic interaction chromatography, affinity chromatography, immunoaffinity chromatography, size exclusion chromatography, liquid chromatography (LC), high performance LC(HPLC), fast performance LC (FPLC), hydroxylapatite chromatography, lectin chromatography, binding to Glutathione-S-Transferase-resin (GST-resin), Maltose-resin and immobilized metal affinity chromatography (IMAC). Generally, the hyperactive reverse transcriptase will be purified by a combination of liquid chromatographic techniques including ion exchange, affinity and size exclusion. When using a tagged fusion protein, the hyperactive reverse transcriptase may be released by, e.g., protease digestion of a linker, addition of a competitor (GST or Maltose), addition of a chelating agent (IMAC) and the like, depending on the system used.

Alternative chromatographic solid supports, mobile phases and associated methods may be equivalently used and will be well-known to one of ordinary skill of protein isolation and purification. The invention thus provides for substantially isolated and purified hyperactive reverse transcriptase. Substantially pure a used herein refers to a preparation or sample which is substantially free of contaminating components, proteins, etc., which may adversely affect the activity or performance of the hyperactive reverse transcriptase in the use of the enzyme such as in amplification or synthesis. If the hyperactive reverse transcriptase if produced as a fusion protein, the skilled artisan may select any of a number of well-known fusion partners, e.g., GST, MBP, FLAG, myc, H is or other tagging methodologies and/or techniques. Depending on the fusion partner and/or tag, the supernatant is loaded on the appropriate column under specific ionic and buffering conditions and the hyperactive RT protein allowed to bind, followed by isolation of the hyperactive RT of, or from, the fusion peptide/protein carrier. For example, in some cases the hyperactive RT remains on the column and the fusion protein/peptide carrier is in the flow-through or vice versa, as will be known to the skilled artisan. In some embodiment, the hyperactive RT may still be used while on or about the resin, that is, as a hyperactive RT resin.

EXAMPLE 5

Measurement of RT-associated RNase H Activities. Characterization of the RNase H activity of the MMLV RT mutants was shown using an assay that reports cleavage of RNA from an RNA:DNA hybrid. Briefly, a hybrid substrate was created by annealing a 1.5 kb RNA with an internal 20-base DNA oligonucleotide to a sequence that is 500 bp from the end of the RNA. Scission of the RNA results in two fragments, 1.0 kb and 0.5 kb, which are resolved and quantified on an RNA LabChip. The assay (5 ul) contains 2 uM DNA, 100 ng/ul RNA, in 1 xRT buffer. RNase H activity of each mutant MMLV RT was compared by monitoring the fraction of cleavage as a function of time.

Table 4 shows the RNase H activity of MMLV RT Mutants. RNase H activity is expressed as the number of polymerase unit enzyme equivalents that achieved 50% cleavage of the RNA:DNA hybrid substrate. In most cases, cleavage was quantified at ~20-35% cleavage (when the assay was truly linear with respect to time and input protein) and extrapolated to 50% to provide a convenient mathematical reference point. ND=Not detected.

TABLE 4

| RNase H Source | # Pol Units to Achieve 50% Cleavage | % of wt-MMLV | (U/ug) Specific Activity* |
|---|---|---|---|
| E. coli RNase H (Ambion-Cloned) | 0.005 | | |
| AMV (Ambion) | 2.0 | 35 | |
| MMLV-RT (Ambion) | 0.7 | 100 | 200 |
| Powerscript (Clontech) 100 U/rxn | ND | <<<<1%** | |
| Superscript II (Invitrogen) 400 U/rxn | ND | <<<<1%** | |
| D524E MMLV RT 5 U/rxn | ND | ~1% | 121 |
| D524N MMLV RT 5 U/rxn | ND | <1% | 147 |
| E562D MMLV RT 5 U/rxn | 23 | ~3% | 135 |
| D653N MMLV RT | 4.5 | 16 | 192 |
| H638G MMLV RT | 5.2 | 13 | 236 |
| F155Y; H638G-MMLV RT | 7.0 | 10 | 240 |
| F155Y MMLV RT | 0.8 | 85 | 240 |

*Units/ug protein.
**No detectable activity.

EXAMPLE 6

Analysis of cDNA Product Synthesis by MMLV RT Mutants. An important property of RT enzymes is that they are able to synthesis cDNA products from mRNA that faithfully maintains the original information content of the transcript. In other words, these enzymes should exhibit a high apparent processivity. Several of the MMLV RT single mutants (D524E, D524N, E562D, H638G, D653N, R301L and F309A) were compared with wild type MMLV-RT (Ambion), wt-MMLV-RT-His and SuperScriptII and III for their ability to make long cDNA products using Ambion's Millenium Marker RNA templates (ranging in size from 0.5 kb to 9.0 kb). The results are shown in FIG. 4, which is a gel that shows a comparison of cDNA product lengths by various mutant MMLV RT enzymes using RNA templates from 0.5 to 9.0 kb in Size.

Briefly, 20 ul reactions included 500 ng of millenium marker and 10 pmole of oligo dT (annealing at 70° C. for 5 min and cool to 42° C.), 250 µM dGTP, dCTP, dTTP, 25 µM dATP, 0.5 µl α-$^{32}$P dATP (3000 µCi/mM), 8 units of RIP and the indicated amount (10 or 100 U) of MMLV-RT enzyme in Ambion's RetroScript buffer. The reaction was incubated at 42° C. for 1 hr and stopped by heating at 95 C for 5 min. A total of 5 µl of sample was mixed with an equal volume of glyoxal loading dye, heated at 50° C. for 30 min, and resolved on 1% Agarose-glyoxal gel. The products were transferred to a nylon membrane prior to exposure to film. Lanes 1 and 11: Ambion MMLV-RT; lanes 2 and 12 MMLV-RT-His; lanes 3 and 13 D524E MMLV RT; lanes 4 and 14 D524N MMLV RT; lane 5 and 15: E562D MMLV RT; lanes 6 and 16: H638G MMLV RT; lanes 7 and 17: D653N MMLV RT; lanes 8 and 18: R301L MMLV RT; lanes 9 and 19: F309A MMLV RT; lanes 10 and 20: SuperScriptII. Lane 18* has only 20 U D653N MMLV RT instead of 100 U owing the lower stock concentration of this mutant.

Other MMLV RT mutants were characterized in similar assays. For example, cDNA products by F155Y MMLV RT, H638G MMLV RT, D524E MMLV RT, D524N MMLV RT, E562D MMLV RT, D653N MMLV RT and the double mutant F155Y;H638G MMLV RT were assayed in a reaction that uses a higher concentration of evenly balanced dNTP's and a single, 9.0 kb RNA template. FIG. 5 is a gel that shows a comparison of cDNA product lengths by various mutant MMLV RT enzymes using a 9.0 kb RNA template. For these reactions, template-primer was incubated for 4 min at 70° C., and then added to the reaction mastermix at 42° C. Reactions were initiated by adding 50 U of enzyme and incubating for 30 min at 42° C. Residual, unhybridized RNA template was removed by treating all reactions with 500 pg/ul bovine RNase A treat in combination with a 1:10,000 dilution of SYBR Gold (to stain the cDNA products). Samples were treated with RNase for 30 min at 37° C. A total of 1 µl of 10×DNA loading dye was added, and one-half of the reaction mixture loaded onto 0.7% agarose gel. The cDNA products were resolved after electrophoresis for 40 min at 90V.

The top half of the gel in FIG. 5 shows the cDNA products with these RT enzymes in a buffer containing 200 ng 9 kb RNA template, 5 uM oligo dT primer, 50 mM Tris pH 8.3, 75 mM KCl, 5 mM DTT, 0.5 mM of each dNTP, 10 U RIP, and 50 U RT enzyme in a 20 ul reaction volume. The bottom half of the gel shows cDNA products from identical reactions, except that 3 mM $MnCl_2$ was used instead of 3 mM $MgCl_2$. This change in the divalent ion changes the product profile significantly, since $Mn^{2+}$ is known to dramatically enhance RNase H activity. As a result, $Mn^{2+}$ causes the cDNA products to be shorter in proportion to the extent of RNase H activity extant in each RT. As a result, those mutants with the greatest amount of RNase H activity make the shortest cDNA products, and those enzymes that have even 10-15% RNase H activity are readily distinguished from enzymes with <1% RNase H activity.

It is significant to note that although the F155Y;H638G MMLV RT mutant fails to demonstrate an increase in this cDNA length assay with this limited length template (9 kb), it was found to outperform all other MMLV RT mutant enzymes in RNA amplification.

EXAMPLE 7

RNA Amplification Properties of MMLV RT Mutants. The RNA amplification reagents used were from Ambion's MessageAmp kit (Ambion, Inc., Austin, Tex., Cat#1750). The reactions were performed according to the instruction manual with 100 units of RT and indicated amount of template. Briefly, the MessageAmp (Ambion, Inc., Austin, Tex.) procedure is based on antisense RNA (aRNA) amplification and involves a series of enzymatic reactions resulting in linear amplification of exceedingly small amounts of RNA for use in array analysis. Unlike exponential RNA amplification methods, such as NASBA and RT-PCR, aRNA amplification maintains representation of the starting mRNA population.

The procedure begins with total or poly(A) RNA that is reverse transcribed using a primer containing both oligo(dT) and a T7 RNA polymerase promoter sequence. After first-strand synthesis, the reaction is treated with RNase H to cleave the mRNA into small fragments. These small RNA fragments serve as primers during a second-strand synthesis reaction that produces a double-stranded cDNA template for transcription. Contaminating rRNA, mRNA fragments and primers are removed and the cDNA template is then used in a large scale in vitro transcription reaction to produce linearly amplified aRNA. The aRNA can be labeled with biotin rNTPS or amino allyl-UTP during transcription. Alternatively, unlabeled aRNA can be used as a template for a reverse transcription with CyDye™-labeled dNTPs to generate labeled cDNA. The RETROscript™ Kit (Ambion, Inc.) may be used for this purpose. For increased yields, the aRNA can also be used as template for cDNA synthesis followed by a second round of amplification using MessageAmp.

Figure 6:
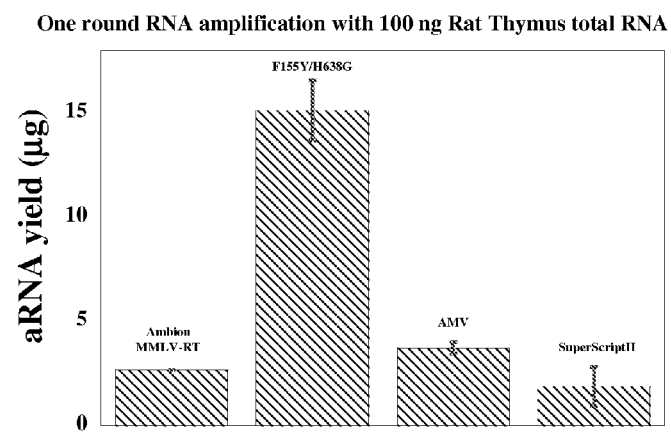
FIG. 6 is a graph that demonstrates single round RNA Amplification with 100 ng Rat Thymus Total RNA: MMLV RT Mutant Comparisons., the aRNA yields were determined by UV absorbance at 260 nm, samples were performed in duplicate.
Figure 7:
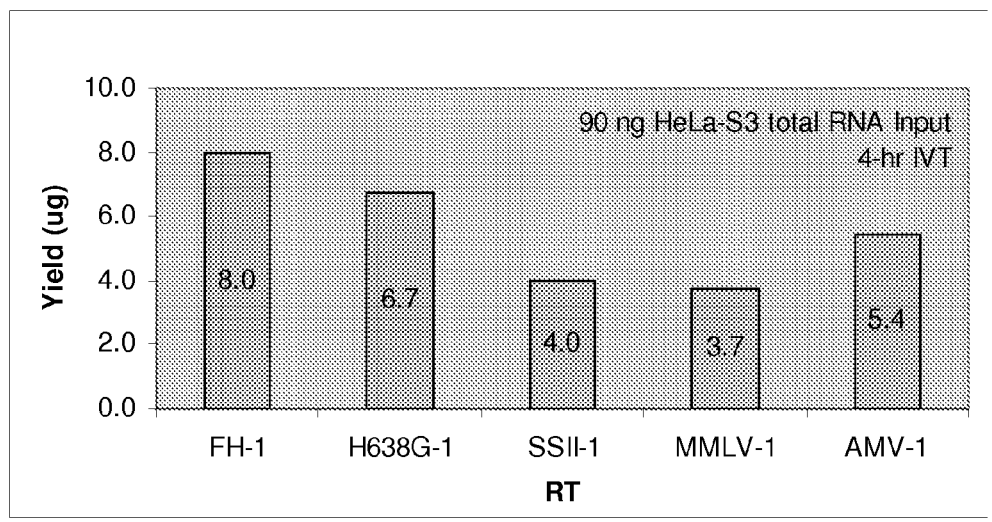
FIG. 7 is a graph of a single round RNA Amplification with 90 ng HeLa S3 Total RNA: MMLV RT Mutant Comparisons (the aRNA yields were determined by UV absorbance at 260 nm, performed in duplicate); FH=F155Y;H638G MMLV RT; SSII=SuperScript II; MMLV=wild-type MMLV RT; AMV=Avian Myeloblastosis Virus RT.

FIG. 6 is a graph of a single round RNA amplification with: (100 ng Rat Thymus Total RNA, comparing different MMLV RT mutants versus wild-type. The aRNA yields were determined by UV absorbance at 260 nm. Samples were performed in duplicate compares the aRNA yields from each of the MMLV RT mutants. Significantly, the double mutant F155Y;H638G MMLV RT produced about 3 to 5 times more aRNA than several other enzymes tested, such as MMLV RT (Ambion), AMV RT (Ambion), and Superscript II (Invitrogen). In a separate study using 100 ng of human HeLa-S3 cell total RNA, the F155Y;H638G MMLV RT produced 1.5 to 2.2 times more aRNA compared to other RTs, including AMV RT and SSII, after one round of amplification. FIG. 7 is a graph of a single round RNA amplification with 100 ng HeLa S-3 Total RNA, again comparing different MMLV RT Mutants versus the wild-type enzyme, and AMV RT. The aRNA yields were determined by UV absorbance at 260 nm and were performed in duplicate. Although the F155Y;H638G MMLV RT produced the most aRNA in this experiment, it is important to note that the single mutant H638G MMLV RT produced almost as much aRNA as the F155Y;H638G double mutant, and thus represents a noteworthy improvement over the currently available reverse transcriptase tools.

Figure 8:
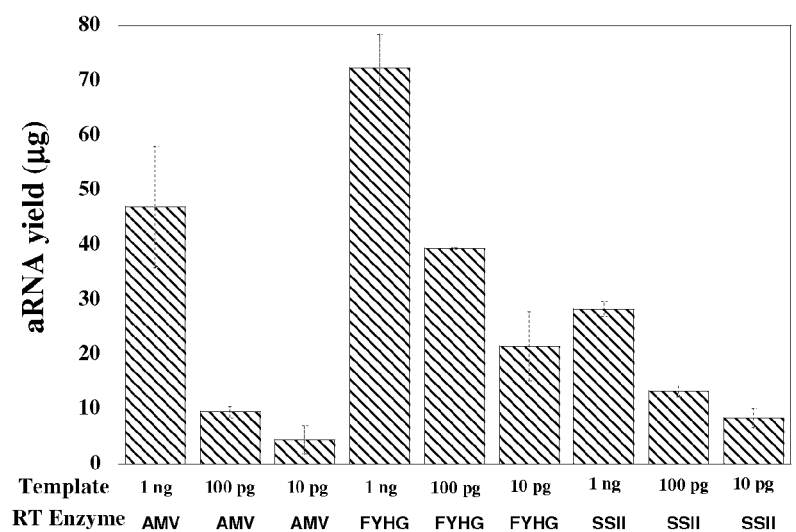
FIG. 8 is a graph that demonstrates the yield from a two round RNA Amplification with 10-1000 pg HeLa S-3 Total RNA: MMLV RT Mutant Comparisons (AMV=Avian Myeloblastosis Virus RT; FYHG=F155Y;H638G MMLV RT; SSII=SuperScript II; The aRNA yields were determined by UV absorbance at 260 nm, performed in duplicate)

Comparable 2- to 4-fold enhancements in aRNA yield by F155Y;H638G MMLV RT were observed in two round RNA amplification reactions, starting with 1 ng, 100 pg, or 10 pg total HeLa-S3 RNA. FIG. 8 is a graph that shows a two round RNA amplification with 10-1000 pg HeLa S-3 Total RNA, again comparing different MMLV RT Mutants versus wild-type. AMV=Avian Myeloblastosis Virus RT; FYHG=F155Y; H638G MMLV RT; SSII=SuperScript II. The aRNA yields were determined by UV absorbance at 260 nm and were performed in duplicate.

In another study, the aRNA yield by F155Y;H638G MMLV RT was compared in MessageAMP with AMV RT using 100 ng and 1 ug input total RNA. As shown in Table 6, F155Y;H638G MMLV RT produced 12% more aRNA from 1 ug of total RNA, and 2.6-fold more aRNA from 100 ng total RNA (both at 200 U F155Y;H638G MMLV RT).

TABLE 5

Yields of aRNA by F155Y; H638G MMLV RT compared to AMV RT at 100 ng and 1 ug of HeLa-S3 Total RNA.

| RT, Units | 1 ug | 100 ng |
| --- | --- | --- |
| F155Y; H638G, 100 U | 56.2 | 6.1 |
| F155Y; H638G, 100 U | 54.1 | 6.6 |
| F155Y; H638G, 100 U | 54.0 | 7.7 |
| F155Y; H638G, 200 U | 66.6 | 17.6 |
| F155Y; H638G, 200 U | 65.8 | 16.2 |
| F155Y; H638G, 200 U | 59.6 | 16.5 |
| Wild-type AMV | 56.8 | 6.2 |
| Wild-type AMV | 57.9 | 6.5 |

Figure 9:
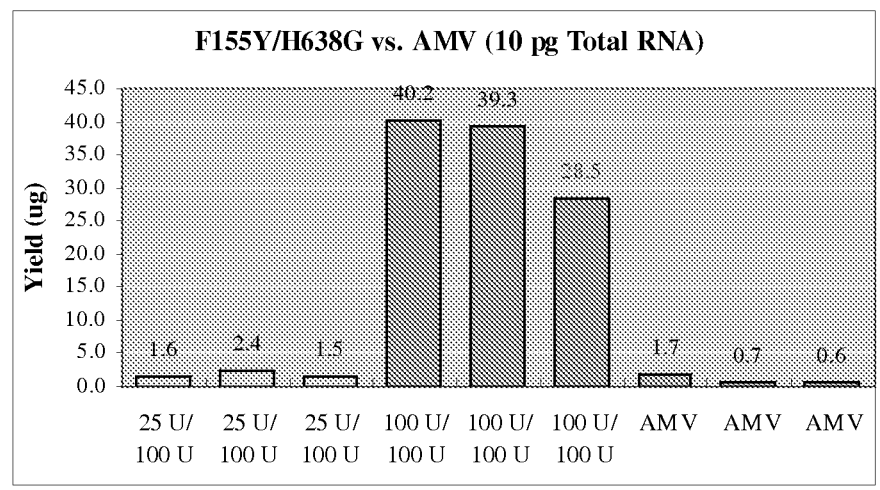
FIG. 9 is a graph that demonstrates the yield from Two Round RNA Amplification Comparing F155Y;H638G MMLV RT and AMV RT (input total RNA was HeLa-S3, at 1 ng and 10 pg)

In another study, the aRNA yield by F155Y;H638G MMLV RT was compared with AMV RT in a two round amplification using MessageAMP using 10 pg input total HeLa-S3 RNA. FIG. 9 is graph that shows the yield from a two round RNA amplification comparing F155Y;H638G MMLV RT and AMV RT. The input total RNA was HeLa-S3, at 1 ng and 10 pg. As shown in FIG. 9, F155Y;H638G MMLV RT produced 22-fold more aRNA than the RT provided in the kit, and nearly 40-fold more aRNA than wild-type AMV RT.

Figure 10:
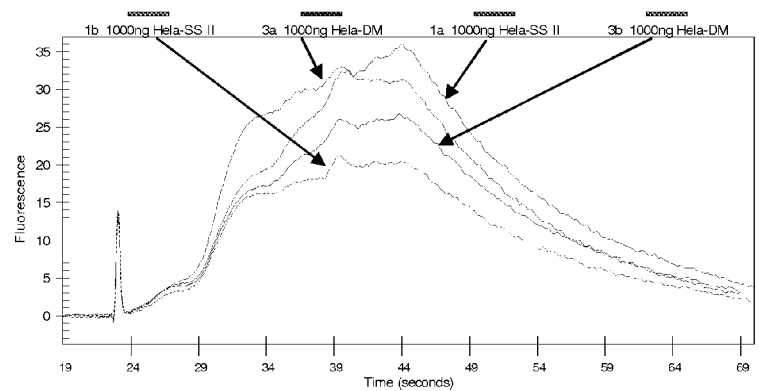
FIG. 10 is a graph that shows compares a hyperactive reverse transcriptase with the Standard Affymetrix aRNA Protocol Comparison to MessageAMP containing F155Y; H638G MMLV RT.

In yet another study, the aRNA yield by F155Y;H638G MMLV RT was compared with the Affymetrix aRNA standard protocol which recommends SuperScript II. In this case, the F155Y;H638G MMLV RT mutant generated 7% more aRNA from 1 ug of total RNA (HeLa-S3), or 20% more aRNA from 100 ng of total RNA, in a single round of RNA amplification. FIG. 10 is a graph that shows a comparison of the present invention with the Standard Affymetrix aRNA Protocol Comparison to MessageAMP containing F155Y; H638G MMLV RT. An input 1000 and 100 ng of HeLa-S3 total RNA was amplified using the Affymetrix aRNA Protocol or Ambion's MessageAMP protocol using F155Y;H638G MMLV RT. aRNA labeling was accomplished through 8 hr biotin CTP/UTP IVT reactions. All reactions were performed in duplicate. Average peak sizes of the aRNA exceed 1700 nucleotides in each case. SSII=SuperScript II; DM=Double mutant, F155Y; H638G MMLV RT. EXAMPLE 8

Figure 11:
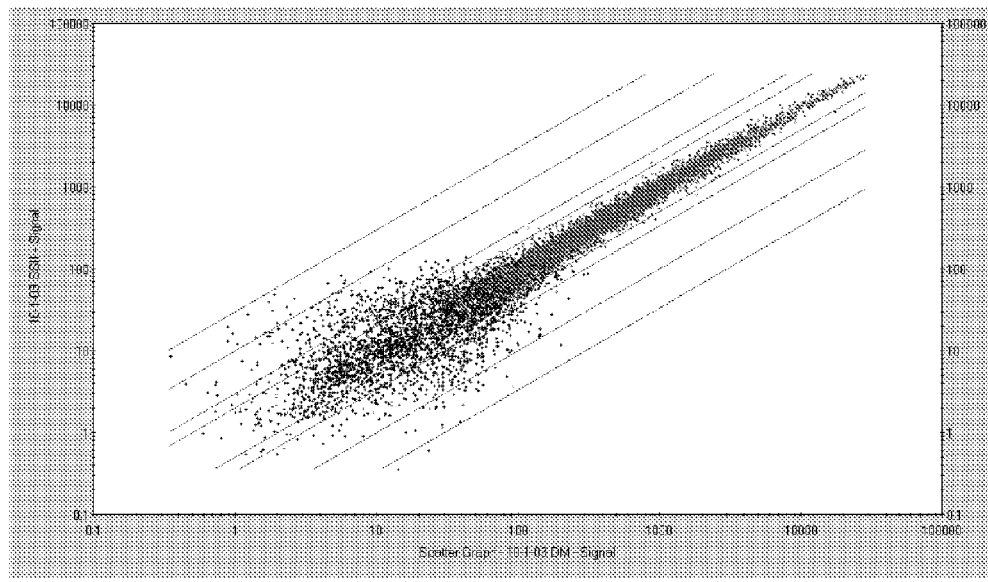
FIG. 11 is a graph that shows a Scatter plot comparing F155Y;H638G MMLV RT (x axis) vs. SSII (y axis) Signal Intensities from a Human Focus Array.

Performance of aRNA produced by F155Y;H638G MMLV RT and SSII on Affymetrix GeneChips. RNA amplified in a single round by F155Y;H638G MMLV RT (using the MessageAMP II protocol (see www.ambion.com)) or the RT provided in the kit (using the Affymetrix aRNA protocol (see www.Affymetrix.com)) was biotin-labeled and hybridized to an Affymetrix Human Focus Array for detection and analysis. The concordance between the two RT enzymes was 93.69% using all 8794 elements on the array. FIG. 11 is a scatter plot of F155Y;H638G MMLV RT (x axis) vs. SSII (y axis) Signal Intensities from a Human Focus Array. The signal intensity correlation is shown. Lines represent 2-, 3-, 10- and 30-fold differences. Red dots are Present-Present calls, Black are Absent-Absent calls, and Dark Blue are Present-Absent (or Absent-Present). This is graph is used to visualize the concordance between arrays. The region on the top, right half contains the P calls (most important). DM=Double Mutant, F155Y;H638G MMLV RT.

Elimination of Absent and Marginal calls increases the concordance substantially. The average signal was 1348 for F155Y;H638G MMLV RT, and 1291 for the Affymetrix standard protocol. Percent present calls were slightly higher for F155Y;H638G MMLV RT than the standard protocol (Table 6), whereas the beta-actin ratio was also slightly more favorable for F155Y;H638G MMLV RT than the RT provided in the kit (Table 7).

TABLE 6

Percent Present Calls on the Human Focus Array by RT Enzyme

| RT Enzyme | % Present Calls |
| --- | --- |
| F155Y; H638G MMLV RT | 54.0% |
| SSII | 53.8% |

TABLE 7

3'/5' Ratios for GAPDH and beta-Actin Genes on the Human Focus Array by RT Enzyme.

|  | SSII | F155Y; H638G MMLV RT |
|---|---|---|
| GAPDH | 0.79 | 0.80 |
| Beta-Actin | 1.24 | 1.12 |

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. An isolated and purified nucleic acid encoding a mutant reverse transcriptase comprising SEQ ID NO:2.

2. The nucleic acid of claim 1, wherein the mutant reverse transcriptase comprises enhanced DNA polymerase activity.

3. The nucleic acid of claim 1, wherein the mutant reverse transcriptase comprises substantially reduced RNase H activity.

4. The nucleic acid of claim 1, wherein the nucleic acid comprises SEQ ID NO.: 1.

5. The nucleic acid of claim 1, wherein the nucleic acid comprises a nucleic acid segment encoding a leader sequence.

6. The nucleic acid of claim 1, wherein the nucleic acid comprises a nucleic acid segment encoding a protein segment other than the mutant reverse transcriptase.

7. A process for making an isolated mutant reverse transcriptase comprising the steps of:
   transforming a host cell with an isolated nucleic acid that encodes a mutant reverse transcriptase comprising SEQ ID NO:2; and
   culturing the host cell under conditions such that the mutant reverse transcriptase is produced.

* * * * *